US011631480B1

(12) United States Patent
Linetsky et al.

(10) Patent No.: US 11,631,480 B1
(45) Date of Patent: Apr. 18, 2023

(54) COMMUNICATIONS SYSTEM, DEVICES, METHODS, AND TECHNIQUES

(71) Applicant: Specialized Communications, Inc., Smithsburg, MD (US)

(72) Inventors: David Linetsky, Hagerstown, MD (US); Timothy Rollins, Hancock, MD (US); Andrew Paul Hoffman, Smithsburg, MD (US)

(73) Assignee: Specialized Communications, Inc., Smithsburg, MD (US)

( * ) Notice: Subject to any disclaimer, the term of this patent is extended or adjusted under 35 U.S.C. 154(b) by 233 days.

(21) Appl. No.: 17/071,541

(22) Filed: Oct. 15, 2020

Related U.S. Application Data

(63) Continuation of application No. 15/227,665, filed on Aug. 3, 2016, now abandoned.

(60) Provisional application No. 62/200,469, filed on Aug. 3, 2015.

(51) Int. Cl.
| | |
|---|---|
| *G06F 3/0481* | (2022.01) |
| *G16H 10/60* | (2018.01) |
| *G16H 40/63* | (2018.01) |
| *G16H 50/30* | (2018.01) |
| *G06F 3/14* | (2006.01) |
| *G06F 40/205* | (2020.01) |

(52) U.S. Cl.
CPC .......... *G16H 10/60* (2018.01); *G06F 3/0481* (2013.01); *G06F 3/14* (2013.01); *G06F 40/205* (2020.01); *G16H 40/63* (2018.01); *G16H 50/30* (2018.01)

(58) Field of Classification Search
CPC ........ G16H 10/60; G16H 50/30; G16H 40/63; G06F 40/205; G06F 3/0481; G06F 3/14
See application file for complete search history.

(56) References Cited

U.S. PATENT DOCUMENTS

| | | | |
|---|---|---|---|
| 7,904,312 B2 | 3/2011 | Denholm | |
| 9,177,465 B2 | 11/2015 | Vanderpohl, III | |
| 10,741,273 B1* | 8/2020 | Kumar | G16H 10/60 |
| 11,309,079 B2* | 4/2022 | Radhakrishnan | G16H 40/63 |
| 2006/0049936 A1 | 3/2006 | Collins, Jr. et al. | |
| 2008/0106374 A1 | 5/2008 | Sharbaugh | |
| 2009/0165207 A1 | 7/2009 | Reed et al. | |
| 2012/0078661 A1 | 3/2012 | Sheldon et al. | |
| 2013/0110547 A1 | 5/2013 | Englund et al. | |
| 2014/0012597 A1 | 1/2014 | Nolte et al. | |
| 2014/0059768 A1 | 3/2014 | Lemire et al. | |

(Continued)

FOREIGN PATENT DOCUMENTS

EP 2660744 A1 6/2013

OTHER PUBLICATIONS

Eriola J. Shanko et al., Real Time Health Monitoring and Wireless Transmission: A Controller Application to Improve Human Medical Needs, Nov. 1, 2013, IEEE Xplore, pp. 1-4 (Year: 2013).*

(Continued)

*Primary Examiner* — Tam T Tran
(74) *Attorney, Agent, or Firm* — Jones Robb, PLLC

(57) ABSTRACT

In general, the systems, components, methods, and techniques provide an automated medical communications system including an automated medical communications board controller device and a medical communications board device providing a medical board communications interface customized for the location of the medical communications board device at the medical facility.

20 Claims, 19 Drawing Sheets

(56) References Cited

U.S. PATENT DOCUMENTS

| | | |
|---|---|---|
| 2014/0096170 A1 | 4/2014 | Emerson et al. |
| 2014/0108023 A1 | 4/2014 | Arkoff |
| 2014/0244298 A1 | 8/2014 | Robinson et al. |
| 2015/0019256 A1* | 1/2015 | Doyle .................... G16H 40/67 705/3 |
| 2015/0170494 A1* | 6/2015 | Hsu ...................... A61B 5/1117 340/539.17 |

OTHER PUBLICATIONS

Mu-Hsuan Wu et al., Design of Technology-Based Self-Service for ICU Patients' Families, Nov. 1, 2009, IEEE Xplore, pp. 1-7 (Year: 2009).*

Manas Bhatnagar,"Design and Evaluation of a Context-Aware User-Interface for Patient Rooms", University of Toronto, 2013, 142page.

Berkowicz et al.,"eWhiteBoard: A Real Time Clinical Scheduler", Laboratory of Computer Science, Massachusetts General Hospital, Boston, MA, 1999,p. 1026.

Aronsky et al.. "Supporting Patient Care in the Emergency Department with a Computerized Whiteboard System, Aronsky et al." J Am Med Inform Assoc. Mar.-Apr. 2008; 15(2): 184-194.

Hertzum et al., "Positive Effects of Electronic Patient Records on Three Clinical Activities"International Journal of Medical Informatics, vol. 77, No. 12, Nov. 2008 pp. 809-817.

France et al., "Emergency physicians' behaviors and workload in the presence of an electronic whiteboard" International Journal of Medical Informatics (2005) 74, 827-837.

\* cited by examiner

| Room # | Patient | Isolation | Fall Risk | OOB Status | Nurse | Contact # | Alarms | | | |
|---|---|---|---|---|---|---|---|---|---|---|
| 5130 | Alex | CDiff | HIGH | 🛏 | Tina | 6845 | | | | |
| 5131 | Charles | - | LOW | 🛏 | Tina | 6845 | | | | |
| 5132 | Gerald | - | LOW | 🚶 | Tina | 6845 | | | | |
| 5133 | Betty | - | HIGH | 🛏 | Tina | 6845 | | | | |
| 5134 | Bobby | Airborne | LOW | 🛏 | Tina | 6845 | | | | |
| 5135 | Gloria | - | HIGH | 🛏 | Tina | 6845 | | | | |
| 5136 | Travis | - | LOW | 🚶 | Tina | 6845 | | | | |
| 5137 | Kristen | Droplet | LOW | 🛏 | Betty | 6820 | | | | |
| 5138 | Ally | - | LOW | 🛏 | Betty | 6820 | | | | |
| 5139 | Tim | - | LOW | 🛏 | Betty | 6820 | | | | |
| 5140 | Eddie | - | HIGH | 🛏 | Betty | 6820 | | | | |
| 5141 | Pablo | - | LOW | 🚶 | Betty | 6820 | | | | |
| 5142 | Andrew | - | LOW | 🛏 | Betty | 6820 | | | | |
| 5143 | Emily | - | LOW | 🛏 | Betty | 6820 | | | | |
| 5144 | David | - | LOW | 🚶 | Rachel | 6815 | | | | |
| 5145 | Beth | - | HIGH | 🛏 | Rachel | 6815 | | | | |
| 5146 | Erin | - | LOW | 🛏 | Rachel | 6815 | | | | |
| 5147 | Robert | Contact | LOW | 🛏 | Rachel | 6815 | | | | |
| 5148 | Keith | - | LOW | 🛏 | Rachel | 6815 | | | | |
| 5149 | Moira | - | LOW | 🛏 | Rachel | 6815 | | | | |
| 5150 | Molly | - | HIGH | 🚶 | Rachel | 6815 | | | | |
| 5151 | Joshua | - | LOW | 🛏 | Danny | 6827 | | | | |
| 5152 | Darnell | - | LOW | 🛏 | Danny | 6827 | | | | |
| 5153 | Jessica | - | LOW | 🛏 | Danny | 6827 | | | | |
| 5154 | Shannel | - | LOW | 🚶 | Danny | 6827 | | | | |
| 5155 | Linda | - | LOW | 🚶 | Danny | 6827 | | | | |
| 5156 | Donald | Contact | HIGH | 🛏 | Danny | 6827 | | | | |
| 5157 | Martin | - | LOW | 🛏 | Danny | 6827 | | | | |

FIG. 12A

| Room # | Patient | Isolation | Fall Risk | OOB Status | Nurse | Contact # | Alarms | | | |
|---|---|---|---|---|---|---|---|---|---|---|
| 5130 | Alex | CDiff | HIGH | 🚶 | Tina | 6845 | | | | |
| 5131 | Charles | - | LOW | 🛏 | Tina | 6845 | | | | |
| 5132 | Gerald | - | LOW | 🚶 | Tina | 6845 | | | | |
| 5133 | Betty | - | HIGH | 🛏 | Tina | 6845 | ■ | | | |
| 5134 | Bobby | Airborne | LOW | 🛏 | Tina | 6845 | | | | |
| 5135 | Gloria | - | HIGH | 🛏 | Tina | 6845 | | | ■ | |
| 5136 | Travis | - | LOW | 🚶 | Tina | 6845 | | | | |
| 5137 | Kristen | Droplet | LOW | 🛏 | Betty | 6820 | ■ | | | |
| 5138 | Ally | - | LOW | 🛏 | Betty | 6820 | | | | |
| 5139 | Tim | - | LOW | 🛏 | Betty | 6820 | | | | |
| 5140 | Eddie | - | HIGH | 🛏 | Betty | 6820 | | | | |
| 5141 | Pablo | - | LOW | 🚶 | Betty | 6820 | | | | |
| 5142 | Andrew | - | LOW | 🛏 | Betty | 6820 | | | | |
| 5143 | Emily | - | LOW | 🛏 | Betty | 6820 | | | | |
| 5144 | David | - | LOW | 🚶 | Rachel | 6815 | | | | |
| 5145 | Beth | - | HIGH | 🛏 | Rachel | 6815 | | | | |
| 5146 | Erin | - | LOW | 🛏 | Rachel | 6815 | | | | |
| 5147 | Robert | Contact | LOW | 🛏 | Rachel | 6815 | | | | |
| 5148 | Keith | - | LOW | 🛏 | Rachel | 6815 | | | | |
| 5149 | Moira | - | LOW | 🛏 | Rachel | 6815 | | | | ■ |
| 5150 | Molly | - | HIGH | 🚶 | Rachel | 6815 | | | | |
| 5151 | Joshua | - | LOW | 🛏 | Danny | 6827 | | | | |
| 5152 | Darnell | - | LOW | 🛏 | Danny | 6827 | | | | |
| 5153 | Jessica | - | LOW | 🛏 | Danny | 6827 | | | | |
| 5154 | Shannel | - | LOW | 🚶 | Danny | 6827 | | | | |
| 5155 | Linda | - | LOW | 🚶 | Danny | 6827 | | | | |
| 5156 | Donald | Contact | HIGH | 🛏 | Danny | 6827 | ■ | | | |
| 5157 | Martin | - | LOW | 🛏 | Danny | 6827 | | | | |

FIG. 12B

| Room # | Next Round | Isolation | Fall Risk | OOB Status | Next Pain Medication | Trending Pain | | Alarms | | | |
|---|---|---|---|---|---|---|---|---|---|---|---|
| 5130 | 10:45 am | Droplet | HIGH | 🛌 | 1:15 pm | 8 | ↕2 | | | | |
| 5131 | *active* | - | LOW | 🛏 | 12:15 pm | 5 | ↕3 | | | | |
| 5132 | 11:00 am | - | LOW | 🚶 | 10:45 am | 1 | ↕1 | | | | |
| 5135 | 4:45 pm | - | HIGH | 🚶 | 1:15 pm | 6 | ↕3 | | | | |
| 5136 | 5:15 pm | Airborne | LOW | 🚶 | 12:15 pm | 8 | ↕2 | | | | |
| 5137 | 2:15 pm | - | HIGH | 🛏 | 10:45 am | 10 | ↕2 | | | | |
| 5138 | 3:15 pm | - | LOW | 🚶 | 10:45 am | 2 | ↕3 | | | | |
| 5139 | 10:45 am | Droplet | LOW | 🚶 | 1:15 pm | 7 | ↕1 | | | | |
| 5130 | 11:15 am | - | LOW | 🛏 | 12:15 pm | 2 | ↕3 | | | | |
| 5131 | 11:00 am | - | HIGH | 🚶 | 10:45 am | 5 | ↕2 | | | | |
| 5132 | 4:45 pm | C-Diff | HIGH | 🚶 | 1:15 pm | 1 | ↕1 | | | | |
| 5133 | 5:15 pm | - | LOW | 🛏 | 12:15 pm | 2 | ↕3 | | | | |
| 5134 | 2:15 pm | - | LOW | 🚶 | 10:45 am | 5 | ↕1 | | | | |
| 5135 | 3:15 pm | - | HIGH | 🚶 | 10:45 am | 5 | ↕3 | | | | |
| 5136 | 10:45 am | Airborne | LOW | 🚶 | 1:15 pm | 1 | ↕3 | | | | |
| 5137 | 11:15 am | - | HIGH | 🚶 | 12:15 pm | 7 | ↕2 | | | | |
| 5138 | 11:00 am | - | LOW | 🚶 | 10:45 am | 8 | ↕3 | | | | |
| 5139 | 4:45 pm | Droplet | LOW | 🛏 | 1:15 pm | 10 | ↕1 | | | | |
| 5131 | 5:15 pm | - | LOW | 🚶 | 12:15 pm | 5 | ↕3 | | | | |
| 5132 | 2:15 pm | - | HIGH | 🚶 | 10:45 am | 6 | ↕2 | | | | |
| 5133 | 3:15 pm | C-Diff | HIGH | 🛏 | 10:45 am | 8 | ↕3 | | | | |
| 5134 | 10:45 am | - | LOW | 🚶 | 1:15 pm | 5 | ↕3 | | | | |
| 5135 | 11:15 am | - | LOW | 🚶 | 12:15 pm | 1 | ↕1 | | | | |
| 5136 | 11:00 am | - | HIGH | 🛏 | 10:45 am | 6 | ↕3 | | | | |
| 5137 | 4:45 pm | Airborne | LOW | 🚶 | 1:15 pm | 8 | ↕2 | | | | |
| 5138 | 5:15 pm | - | HIGH | 🚶 | 12:15 pm | 5 | Initial Pain Level | | | | |
| 5139 | 2:15 pm | - | LOW | 🛏 | 10:45 am | 1 | ↕3 | | | | |
| 5139 | 3:15 pm | Droplet | LOW | 🛏 | 10:45 am | 4 | ↕2 | | | | |

FIG. 12C

COMMUNICATIONS SYSTEM, DEVICES, METHODS, AND TECHNIQUES

CROSS-REFERENCE TO RELATED APPLICATIONS

This application is a continuation of U.S. patent application Ser. No. 15/227,665 titled "AUTOMATED MEDICAL PATIENT COMMUNICATIONS SYSTEM, DEVICES, METHODS, AND TECHNIQUES" filed Aug. 3, 2016, which claims the benefit under 35 U.S.C. § 119(e) of U.S. Provisional Application No. 62/200,469, titled "AUTOMATED MEDICAL DIGITAL WHITEBOARD & PATIENT SAFETY SYSTEMS, METHODS, AND TECHNIQUES" filed on Aug. 3, 2015 in the U.S. Patent and Trademark Office, both of which are herein expressly incorporated by reference in their entirety for all purposes.

BACKGROUND

Technical Field

In general, the following application describes an automated medical communications board controller device and a medical communications board device system and related systems, device, methods, and techniques.

Related Art

Hospitals and other medical care facilities have continued to focus on improving patient safety, care, and satisfaction. Hospitals are dissatisfied with high litigation costs and increased insurance premiums related to patient injuries that are the result of staff error (e.g., patient falls and their related injuries). In addition, hospitals also are dissatisfied with poor performance and evaluations provided by patients, as these evaluations affect hospital ratings. Ratings in turn affect operational costs, revenue, funding, donations, and attraction of and/maintaining talented staff and doctors.

In order to convey information to patients about their stay, hospitals employ in-room, dry-erase whiteboards to communicate information to the patient. However, as anyone who has spent any time in a hospital knows, these whiteboards are notoriously left blank or worse contain outdated, incomplete, and/or incorrect information. For example, in many instances the only information provided on the whiteboard is a nurse's name, despite having areas labeled for other information. Many times, when information is provided, the information is not regularly updated resulting in confusion for many patients and their families. In addition, when incorrect information is displayed patients become confused and dissatisfied, and often feel neglected leading to poor evaluations. Moreover, incorrect information can lead to unsafe or hazardous conditions that affect patient safety and wellbeing.

Unfortunately, nurses tasked with writing down information on whiteboards simply do not have time to fill out the whiteboards properly, and hospitals do not have budgets to hire the additional nurses required to correctly maintain these boards or pay nurses for the additional time necessary to provide this service. When given a choice between the medical tasks required of a nurse, filling out the whiteboard remains a very low priority for most nurses. As a result, most whiteboard initiatives fail soon after implementation because it is impossible to keep up with the workload required for proper maintenance of the boards.

Hospitals are overwhelmingly aware of the positive effects of properly filled out patient room whiteboards and continue to implement whiteboard initiatives even though these initiatives eventually fail. Hospitals continue in this futility because whiteboards offer undeniable benefits and no other solution exists. However, most hospitals do not appreciate the negative effects of blank or incorrectly filled out whiteboards, which can severely harm a hospital's patient evaluation and ratings.

Limited attempts have been made to introduce electronic whiteboards; however, like their dry-erase cousins, these whiteboards also fail for the exact same reasons. Nurses simply do not have time to enter in additional information and information still is omitted, forgotten, or incorrectly entered leading to patient and family confusion, dissatisfaction, or unsafe conditions.

SUMMARY

In general, the following description relates to an automated medical patient communications system including an automated medical communications board controller and medical communications board device providing a medical communications interface that leverage existing medical facility systems and patient devices to accurately and automatically provide an interface customized for different aspects of patient care. These systems automatically determine potentially hazardous conditions and notify patients and caretakers of the potentially hazardous conditions to protect and improve care of patients regardless of the existing or enterprise hospital systems and/or protocols while keeping patients informed about their stay in a medical facility. Implementations of any of the described techniques may include a method or a process, an apparatus, a device, a machine, one or more systems, in addition to instructions stored on a non-transitory computer-readable storage device, as explained in detail below.

In one general aspect, an automated medical communications system includes an automated medical communications board controller device and a medical communications board device. The automated medical communications board controller device includes: a board controller network communications interface device receiving data packets from: a first data source including patient health records for patients at a medical facility, and a second data source including a reading or a setting from a patient device corresponding to a patient or a patient location of the medical facility; a storage device storing a medical communication interface storage structure comprising: patient information; medical device information; and a medical board communications interface template; and a board controller device, operatively connected to the board controller network communication interface and the storage device, wherein the board control device performs the operations comprising: parsing the received data packets to extract information according to the source of the information; controlling the storage device to store the extracted information from the data packets in the medical communication interface storage structure as the patient information and the medical device information according to the source of the information; determining a hazardous patient safety condition exists from the patient information received from the first source in combination with corresponding medical device information from the second source; accessing the medical board communication interface template; assembling a content payload designated by the template for a medical board communications interface customized for a location at the medical facility using the patient information and the medical device information, wherein the medical board communications interface includes content indicating the hazardous safety condition; generating a communication package including the content payload for the assembled medical board communications interface, wherein the an automated communications medical board controller transmits the communication package. The medical communications board device includes: a medical board network communications interface receiving the communication; a digital display; a medical board control device operatively coupled to the medical board communications interface and the digital display, wherein the medical board control device performs the operations comprising: determining the communication package is addressed to the medical communications board device; unpacking the communication package to access the content payload; rendering the content payload on the digital display as the medical board communications interface customized for the location of the medical communications board device at the medical facility, wherein the rendered content includes patient information, corresponding medical device information, and an indication of the hazardous safety condition.

The first source may be an electronic health records system of the medical facility and the second source may be a patient device or a patient device controller that is electronically subscribed to by the automated medical communications board controller device.

The patient device may be a patient bed.

The automated medical communications board controller device may implement a patient safety protocol and the operation of determining a hazardous patient safety condition exists includes: accessing the medical device information; determining a patient corresponding to the medical device information; accessing patient information from the medical communication interface storage structure corresponding to the determined patient; determining that a reading or a setting of the medical device in combination with the corresponding accessed patient information indicates a condition of the patient or the patient's environment for alerting medical staff of the facility of the condition; and providing an indication corresponding to the medical alert condition as content for assembly in the content payload.

The patient information may include identification of a fall risk for the patient and the medical alert condition may include one of: a failure to arm a bed exit alarm; an improper bed height; a patient out of bed alert; a failure to position a bed rail, and a failure to set a bed brake.

The patient information may include identification of intubation of the patient and the medical alert condition may include an improper Fowler position of the patient's bed.

The patient information may include identification of a fall risk for the patient, the reading is a weight measurement, the medical alert condition may be a patient out of bed alert.

The system may further include a plurality of a medical communications board devices, wherein the medical communication interface storage structure further include: a plurality of medical board communications interface templates; and assembling the content payload includes assembling a content payload designated by a first template for a medical board communications interface customized for understanding by a patient or person without medical training and assembling a content payload designated by a second template customized for understanding by staff of the medical facility, and the medical communications board controller device transmits the first content payload addressed to a first medical communications board device located in the patient's room and the second content payload addressed to a second medical communications board device located at a monitoring station of the medical facility.

The system may further include a plurality of a medical communications board devices, wherein the medical communication interface storage structure further includes: a plurality of medical board communications interface templates; and assembling the content payload includes assembling a content payload designated by a first template for a medical board communications interface customized for a first location and assembling a content payload designated by a second template customized for a second location, and the medical communications board device board controller device transmits the first content payload addressed to a first medical communications board device located in the patient's room and the second content payload addressed to a second medical communications board device located outside the patient's room.

The template may have corresponding, customizable display widgets that associate data from the medical communication interface storage structure to assemble the medical board communications interface corresponding to the template.

The template may correspond to one of a medical board communications interface customized for a location at the medical facility including: a medical communication board associated with the patient location; a medical communication board associated with the outside the patient location; and a medical communication board associated with a monitoring station at a medical facility tasked with caring for the patient.

In another general aspect, an automated medical communications board controller device includes a board controller network communications interface device operable to receive data packets from: a first data source including patient medical records for patients at a medical facility, and a second data source including a reading or a setting from a patient device corresponding to a patient or a patient location of the medical facility; a storage device operable to store a medical communication interface storage structure including: patient information; medical device information; and a medical board communications interface template; and a board controller device, operatively connected to the board controller network communication interface and the storage device, wherein the board control device is operable to perform the operations comprising: parsing the received data packets to extract information according to the source of the information; controlling the storage device to store the extracted information from the data packets in the medical communication interface storage structure as the patient information and the medical device information according to the source of the information; determining a hazardous patient safety condition exists from the patient information received from the first source in combination with corresponding medical device information from the second source; accessing the medical board communication interface template; assembling a content payload designated by the template for a medical board communications interface customized for a location at the medical facility using the patient information and the medical device information, wherein the medical board communications interface includes content indicating the hazardous safety condition; generating a communication package including the content payload for the assembled medical board communications interface, wherein the an automated communications medical board controller transmits the communication package to at least one medical communications board device at the medical facility.

The first source may be an electronic health records system of the medical facility and the second source may be a patient device or a patient device controller that is electronically subscribed to by the automated medical communications board controller device.

The patient device may be a patient bed.

The automated medical communications board controller device may be operable to implement a patient safety protocol and the operation of determining a hazardous patient safety condition exists includes: accessing the medical device information; determining a patient corresponding to the medical device information; accessing patient information from the medical communication interface storage structure corresponding to the determined patient; determining that a reading or a setting of the medical device in combination with the corresponding accessed patient information indicates a condition of the patient or the patient's environment for alerting medical staff of the facility of the condition; and providing an indication corresponding to the medical alert condition as content for assembly in the content payload.

The patient information may include identification of a fall risk for the patient and the medical alert condition may include one of: a failure to arm a bed exit alarm; an improper bed height; a patient out of bed alert; a failure to position a bed rail, and a failure to set a bed brake.

The patient information may include identification of intubation of the patient and the medical alert condition may include an improper Fowler position of the patient's bed.

The patient information may include identification of a fall risk for the patient, the reading is a weight measurement, and the medical alert condition may be a patient out of bed alert.

In yet another general aspect, a medical communications board device includes: a medical board network communications interface operable to receive a communication from an automated medical communications board controller device, the communication including a content payload generated by the automated medical communications board controller device from a medical board communications interface template customized for a location at a medical facility using information from a first data source including patient medical records for patients at a medical facility, and a second data source including a reading or a setting from a patient device corresponding to a patient or a patient location of the medical facility, the content including an indication that a hazardous patient safety condition exists as determined from the patient information received from the first source in combination with corresponding medical device information from the second source; a digital display; a medical board control device operatively coupled to the medical board communications interface and the digital display, wherein the medical board control device is operable to perform the operations comprising: determining the communication package is addressed to the medical communications board device; unpacking the communication package to access the content payload; rendering the content payload on the digital display as the medical board communications interface customized for the location of the medical communications board device at the medical facility, wherein the rendered content includes patient information, corresponding medical device information, and an indication of the hazardous safety condition.

The content payload may be customized for a location at the medical facility, the location at the medical facility including one of: a medical communication board associated with the patient location; a medical communication board associated with the outside the patient location; and a medical communication board associated with a monitoring station at a medical facility tasked with caring for the patient.

The content payload for the medical board communications interface may be customized for the location of the medical communications board device at the medical facility to provide a communications interface customized for understanding by a patient or person without medical training when the board is located at the patient's location and to provide a communications interface customized for understanding by medical staff of the facility when the board is located outside the patient's location.

The details of particular implementations are set forth in the accompanying drawings and description below. Other features will be apparent from the following description, including the drawings, and the claims.

BRIEF DESCRIPTION OF THE DRAWINGS

FIGS. 12A, 12B, and 12C are examples of a nurse station patient digital whiteboard interface.

Throughout the drawings and the detailed description, the same reference numerals refer to the same elements. In addition, the drawings may not be to scale, and the relative size, proportions, and depiction of elements in the drawings may be exaggerated for clarity, illustration, and/or convenience.

DETAILED DESCRIPTION

Figure 1:
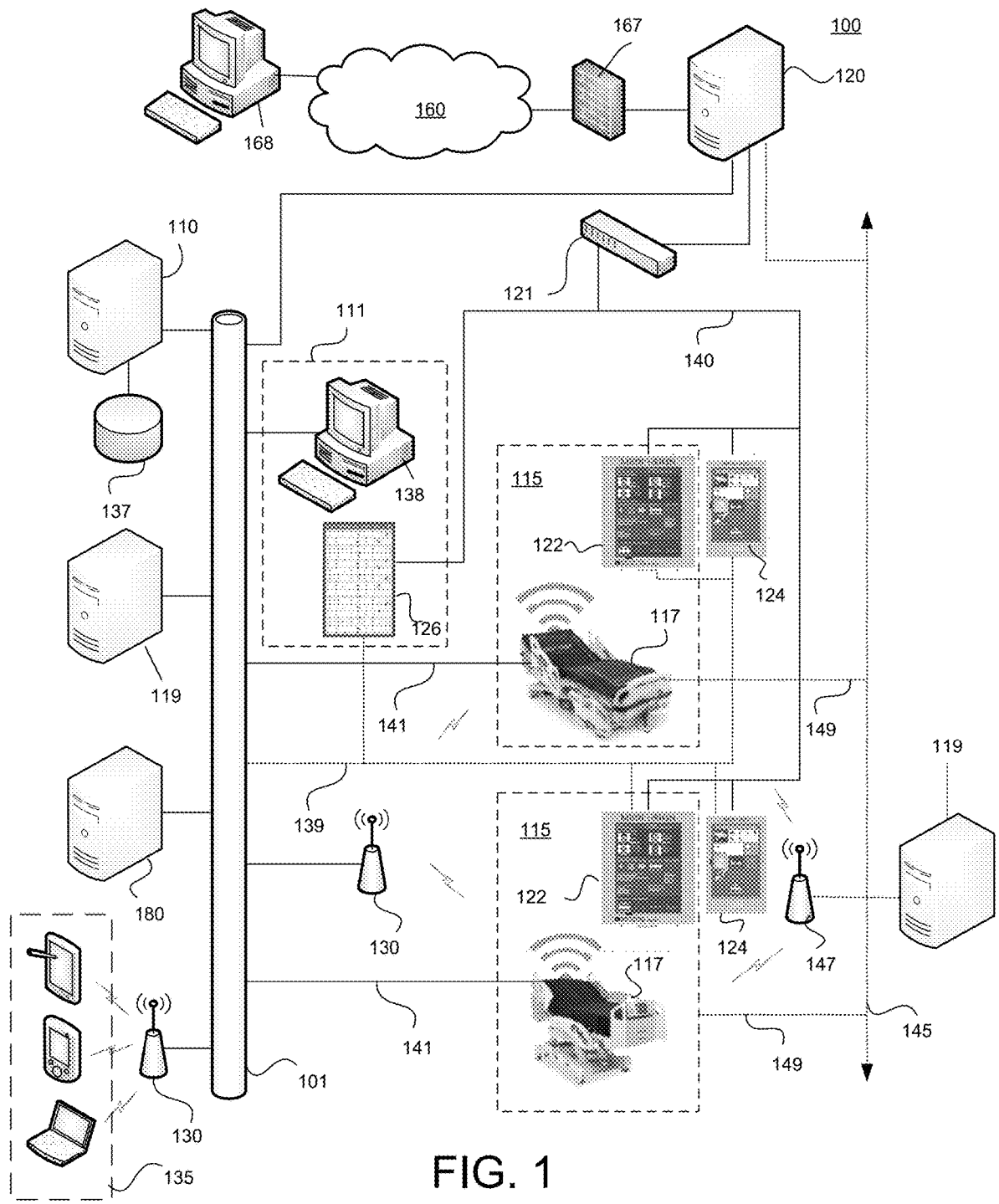
FIG. 1 is a block diagram illustrating an example of a patient digital whiteboard and safety system for optimizing and facilitating patient safety and display of accurate patient information.

The following description relates to an automated medical patient communications system including an automated medical communications board controller and medical communications board device providing a medical communications interface that leverage existing medical facility systems and patient devices to accurately and automatically provide an interface customized for different aspects of patient care. These systems automatically determine potentially hazardous conditions and notify patients and caretakers of the potentially hazardous conditions to protect and improve care of patients regardless of the existing or enterprise hospital systems and/or protocols while keeping patients informed about their stay in a medical facility. Implementations of any of the described techniques may include a method or a process, an apparatus, a device, a machine, one or more systems, in addition to instructions stored on a non-transitory computer-readable storage device, as explained in detail below. The details of particular implementations are set forth in the accompanying drawings and description below. Other features will be apparent from the following description, including the drawings, and the claims.

The medical communications interface and systems, processes, and techniques provided herein allow medical professionals and nurses to provide bedside care while removing the labor-intensive and tedious task of maintaining whiteboards. Moreover, the systems, processes, and techniques as described herein provide a technical solution to automating and integrating various and disparate medical facility systems, patient devices, and protocols to assemble digital, customizable communications interfaces that separately provide varying content in a manner tailored for patients, family and friends, and hospital staff. All of the communication interfaces provide customizable content that is current, accurate, and does not require any additional nurse (or other care personnel) interaction or upkeep to maintain its functionality. Because of this technical solution to the problems faced by traditional whiteboard initiatives, medical facilities can save millions in labor costs while actually achieving the goals set forth by their whiteboard initiatives. In addition, the communication interfaces also provide a technical solution to the current unreliable and inefficient care methods found in medical facilities by providing automated communications translated into formats that are understandable by both patients and staff to prevent. For example, the system automatically can aggregate and assemble a data storage structure form different existing medical care facility systems and patient devices and then implement safety protocols using a combination of information from these systems and devices to automatically trigger alert conditions. This solution reduces, mitigates, and or corrects errors by medical staff that led to litigation and rising insurance premiums by automatically providing accurate data and automated safety alerts that are otherwise not currently available to medical facility staff and patients and thereby prevent accidents or harm to patients from occurring.

Moreover, current systems and protocols require additional work by nurses and care staff to manage the patient, which can lead to errors, including errors of omission (such as failing to follow the existing protocol), safety hazards, and potential harm. For example, in many instances nurses and staff simply do not manage this work at all, which leaves patients guessing or frustrated and safety hazards to persist. In general, the communications system provided herein provides a technical solution to these and other problems by providing an automated patient digital whiteboard system with customized communications interfaces that provide both patient and staff facing interfaces. The patient interface communicates with patients and their families keeping them well informed, educated, and safe during their stay. As a result, this technical solution empowers patients to monitor and provide for their own safety and care. The system also includes an automated interface control system that integrates existing medical care facility systems with patient devices to monitor patients, automatically assemble, and provide accurate content for caregiver communication interfaces that alert staff to safety hazards and potentially dangerous situations on a real time, automated basis without any additional input or maintenance by the hospital staff. The caregiver communications interfaces may be presented by a patient digital door board and a monitoring station digital board. This technical solution eliminates the need for management by nurses and caregivers reducing errors, improving content, and alerting staff to previously unknown or detectable safety issues, hazards, and conditions so that they can be resolved before harm to the patient occurs.

The automated patient digital whiteboard is a hospital grade device that, for example, incorporates a display, an ambient light sensor, and other technology in an enclosure that is customizable in size and décor, and is designed to be installed inside a patient's room. The automated patient digital whiteboard automatically provides a user communications interface presenting information regarding a patient's stay using a processing system that automatically aggregates, parses, and processes multiple sources of hospital data to assemble and generate the interface with content translated for the patient that is accurate and up-to-date. The automated patient digital whiteboard is able to display customizable, pertinent content that is individualized for the patient in the room. Nurses', aides', therapists' and doctors' names assigned to the patient for a shift are displayed along with their photographs. In addition, other content is presented, such as, for example, mobility status, plan for the day, medication precautions, among others. Information can be displayed in multiple languages according to a patient's preferred language.

A corresponding patient digital door board is mounted outside of a patient's room. The patient digital door board provides a user communications interface that displays content traditionally presented using a paper sign or reversible plastic strips that are placed on the wall or the door of the patient's room. The displayed content is fully customizable and may include, for example, whether the patient has contact restrictions, is a fall risk, the patient's preferred language, allergies, and alarms that are automatically updated and accurate, among other content.

An additional monitoring station digital board is used to display nurse assignments, round times, medication times, patient information, and safety conditions and notifications, such as alarms.

There are a number of advantages and benefits to the technical solutions provided by the systems and techniques described herein. For example, no training or extra work for medical staff is required by the communications system thereby saving thousands of labor hours per year. This in turn allows nurses to spend more time focusing on patients. In addition, patient/staff awareness and quality of care is increased. The system improves patient communication and evaluations (e.g., HCAHPS) helping to generate a positive reputation for the facility. The system is fully automated by connecting to existing medical databases, electronic health records, and patient devices and uses existing network infrastructure of the medical facility. The system automatically integrates these disparate types of systems and their protocols or formats, which are not otherwise able to communicate with each other and leverages the existing infrastructure to automatically aggregate, process, assemble, and build the communication interfaces for both the patient and medical facility workers. One result is that the system is able to warn of potential hazards and dangerous conditions that were previously unknown or unable to be monitored. These interfaces also allow both patients and staff to monitor and prevent harm that might otherwise come to patients using existing medical facility apparatus and protocols. In addition, the solution is scalable for easy future expansions as needed. Furthermore, content and layout are fully customizable for the particular application or medical facility.

Automated Medical Patient Communications and Monitoring System

FIG. 1 shows a block diagram illustrating an example of an automated medical patient communications system for optimizing and facilitating patient safety and communication with patients. As shown in FIG. 1, the system 100 includes a number of components for a medical facility including: a medical facility communications network 101, a patient electronic health records system 110, one or more patient monitoring stations 111, two or more patient rooms 115, and two or more patient health devices 117. In addition, the system includes one or more patient device systems 119. As shown, the system 100 also includes an automated medical interface and communications (AMIC) system including an automated medical board controller device 120, an AMIC network 121, automated medical communications board devices, such as patient digital whiteboards 122, patient digital door boards 124, and a monitoring station digital board 126. In one example, the medical facility is a hospital or other facility administering medical procedures and/or providing care for patients.

As shown in FIG. 1 various components of the system 100 exchange data using the medical facility network 101. In one example, the medical facility network is a local area network (LAN) that provides Ethernet over twisted pair cabling and Wi-Fi for transmission of data between components. The network may include one or more wireless access points (WAPs) 130 that allow one or more hospital wireless devices 135 to communicate using the network. For example, tablets, personal data assistants, smart phones, and laptop and/or notebook computers used by medical staff, such as doctors, nurses, and administrators may communicate wirelessly with the medical facility network. Data and content may be exchanged between the various system components through a communications interface communicating with the network using any one of a number of communications protocols corresponding to the different media delivery platforms.

In one example, data may be exchanged employing a protocol used for communicating data across a packet-switched network using, for example, the Internet Protocol Suite, also referred to as TCP/IP. The data and content may be delivered using datagrams (or packets) from the source host to the destination host solely based on their addresses. For this purpose, the Internet Protocol (IP) defines addressing methods and structures for datagram encapsulation. Examples of an Internet protocol include Internet Protocol Version 4 (IPv4) and Internet Protocol Version 6 (IPv6). Of course, one will appreciate that other and/or additional communication protocols may be used to exchange data.

In addition, networks other than LANs may be used to implement the medical facility network. For example, a wide area network may be used in a setting where a hospital or institution is provided over a larger area, such as a campus, a region, or even at distributed geographical locations. The medical facility network may include various components, such as network interface cards, fiber media converters, servers, routers, switches, hubs, bridges, repeaters, gateways, modems, processors, and storage devices. Additional examples are provided below.

The system 100 includes a patient health records system 110 for managing patient health records. The patient health records system includes at least one computing system including at least one processing device. For example, the computing system may be a server running applications with one or more communications interfaces, such as a network card that allows the server to send and receive data on the medical facility network. The computing system also includes at least one storage device. The storage device includes one or more databases that store patient information. One or more additional storage devices 137 may backup information stored in the databases. The backup information and databases may be stored on site at the facility, remotely at one or more offsite locations, or both.

In one example, the storage device stores patient health records, such as an electronic health record (EHR), or electronic medical record (EMR), or any other record, which provides for the systematic collection of patient and population health information stored electronically in a digital format. The records can be shared across different health care settings. Records are shared through network-connected, enterprise-wide data systems or other data networks and exchanges. EHRs, EMRs, and health records in general may include a range of data, including demographics, medical history, medication and allergies, immunization status, laboratory test results, radiology images, vital signs, personal statistics like age and weight, and billing information.

In particular, when a patient is admitted to the hospital or medical facility, an electronic record with the patient's information is generated (if not in existence) or is accessed and updated. In addition, during a patient stay at the facility, the patient records are updated according to the care, tests, measurements, treatments, procedures, and diagnosis provided to the patient. The records may be updated according to data entered by medical staff (e.g., nurses and doctors) and facility administrators at various times throughout a patient stay as part of the normal procedures and protocols of the facility. Patient records are stored in a database structure using, for example, a standard query language (SQL) that manages a relational database and controls reading, writing, modifying, and processing the information stored in the databases. In addition, the EHR server may include software other than interfaces with the health records. For example, the server may employ a health level 7 (HL7) standard compliant database, which provides for standardized patient data stored in the electronic health records. Other examples of database technology that may be used include MEDITECH, CERNER, EPIC and other SQL, MYSQL, ORACLE or ODBC-compliant database systems.

The system 100 includes one or more patient monitoring stations 111. The patient monitoring station is typically located near a corresponding patient area for monitoring patients and is typically staffed by medical personnel that are responsible for a patient's care, such as nurses and doctors, among others. Each patient area includes a number of patient locations 115 where patients stay. Patient areas may be organized by floor or location in a hospital, by medical discipline, and/or by type of care provided. For example, patient areas and locations include bays in an emergency department (ER) or an intensive care unit (ICU) (e.g., pediatric, neonatal, and cardiovascular) or rooms in a ward, such as cardiology, neurology, oncology, obstetrics and/or gynecology. The patient monitoring station includes one or more workstations 138 (or other computing devices) to provide access to the medical network by health care workers (such as doctors and nurses) in charge of a body of patients. The workstation may be used to access medical records and enter information about the patient including chart information among other things.

The patient monitoring station also includes a monitoring station digital board 126. The monitoring station digital board provides a medical communications interface that automatically provides up-to-date and/or real time content about patients that is customized for medical health care workers. Examples of patient content include a location, a patient identifier, a nurse identifier and contact number, a next round time, a next medication time, patient information, and alarms and/or other notifications. In one example, the location identifies the location of the patient in the hospital, such as a room number. The patient identifier may be a name of a patient. The nurse identifier may be a name, and the contact number may include an extension at which the nurse may be reached. The next round time may indicate a future time at which the nurse should visit the patient or an indication that the nurse's round is past due. The next medication time may indicate a future time at which medication (e.g., pain medication) should be administered to the patient or an indication that the medication is past due. The patient information may include information about a patient, such as, for example, whether the patient is in isolation or a fall risk. The patient information also may include one or more indications of trending pain, such as a current pain level (e.g., a number), a difference from the last pain level (e.g., a number indicating the increase or decrease from the previously measured/indicated pain level) and an indication of the direction of increase or decrease (e.g., one or more of a direction such as an arrow and a color e.g., red for increasing and green for decreasing, and an indication that the pain level is the initial pain level). The alarms may include information about a patient device, for example, and include a bed alarm, a rail position, a bed height, a bed brake setting, a Fowler position, and whether a patient is out of bed.

The monitoring station digital board may be connected to the automated medical communications board controller device through a connection to the private display network 121 or through an optional connection 139 to the medical facility network. The monitoring station digital board receives display content through one of the networks from the automated medical communications board controller device and renders the received content. The monitoring station digital board displays real-time content for each patient including important safety information (e.g., fall prevention information for each bed including critical bed configuration and out of bed status). The monitoring station digital board receives the content without any additional input required by the medical health care workers at the station. As a result, the monitoring station digital board provides at-a-glance, automated insight into a patient's state that fosters an environment of safety and healing. The monitoring station digital board is described in further detail below in relation to FIGS. 2 and 3 and examples of a display are shown in FIGS. 12A, 12B, 12C.

In one example, a patient area includes two or more patient locations 115, such as a room, where the patient is assigned during their stay at the facility, such as a hospital. The patient location includes at least one patient health device 117, an automated patient digital whiteboard 122, and a patient digital door board 124.

A patient health device may include any electronic device assigned to patient care and/or monitoring that has data communication capabilities and a location identifier. In one example, a patient health device is a patient bed system. Other examples of patient health devices include patient monitoring and/or vital sign systems, telemetry systems, patient transportation systems, operating room systems, an infusion pump, and/or a medication dispensing system. In this example, the patient bed system includes a number of different sensors, which provide data about the bed and patient. For example, data may include an identifier, a location, an alarm status, a bed rail position, a bed height, a bed Fowler position, a weight, a brake setting, an exit alarm setting, among others. In one example, the data is communicated to a patient device system using the medical facility network (e.g., either wirelessly using a WAP 130 or directly through a wired Ethernet connection 141), or optionally through a private network 145 (e.g., either wirelessly using a WAP 147 or directly through a wired Ethernet connection 149).

The patient device system 119 is implemented using a processing device, a storage device, and communications interface that receives data using the medical facility network or the private network. In one implementation, the patient device system may be a server connected to the medical facility network or a private network that exchanges data with or issues instructions to a patient health device. The patient device system may store data regarding the patient health devices and issue instructions to the patient health devices. The patient device system can send data to other systems through a network connection (e.g., the medical facility network 101 or private network 145). For example, the automated medical communications board controller device can subscribe to a patient device system and receive information about a patient health device corresponding to a desired location 115. An example of one implementation of a patient device system and patient health device using a patient bed system and patient beds are described in U.S. application Ser. No. 13/775,285 filed Feb. 25, 2015 and titled "Hospital Bed," which is herein incorporated by reference in its entirety. Furthermore, a detailed example of a patient device system and patient health device system is provided below in in relation to the description of FIG. 4.

As shown in FIG. 1, the patient location also includes an automated patient digital whiteboard 122. The automated patient digital whiteboard is a hospital grade device that incorporates a backlit display, an ambient light sensor, and other technology in an enclosure. The automated patient digital whiteboard is customizable in size and décor and, in one example, is designed to be installed in a patient's room. The automated patient digital whiteboard includes a processing device that presents content provided from the automated medical communications board controller device. The content presented by the automated patient digital whiteboard may be customized, pertinent information that is individualized for the patient assigned to the location. For example, Nurses', aides', therapists' and doctors' names, along with their pictures, assigned to the patient for that shift are displayed, as well as, mobility status, plan for the day, medication precautions, among others. In addition, preselected information can be displayed in other languages when patient's preferred language is provided to the automated medical communications board controller device. The automated patient digital whiteboard is described in further detail below in relation to FIGS. 2 and 3 and examples of a display are shown in FIGS. 10A, 10B, 10C, and 10D.

Figure 11A:
FIGS. 11A, 11B, and 11C are examples of an exterior door patient digital whiteboard interface.
Figure 11B:
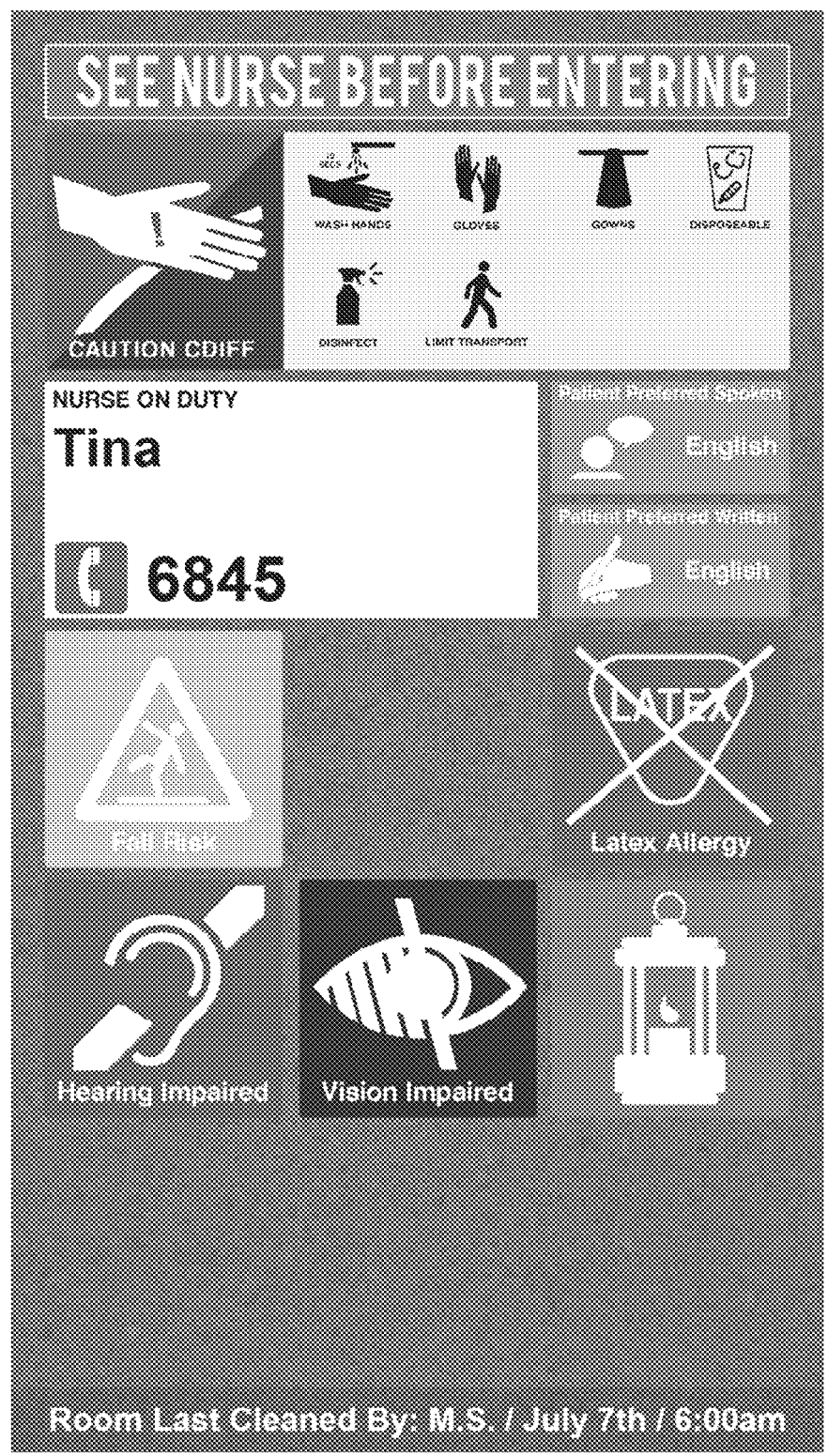

As shown in FIG. 1, the patient location also includes a patient digital door display 124. The patient digital door display is another display version of the automated patient digital whiteboard that is mounted outside of the patient location. The patient digital door display presents content that is traditionally provided for a patient location using a paper sign or reversible plastic strips that are placed on the wall or the door of the patient's room. The patient digital door display also includes a processing device that presents content such as, for example, a fall risk, a preferred language, latex or other allergies, and patient health device alarms, which are automatically provided by the automated medical communications board controller device. The content presented by the patient digital door display is fully customizable as explained below. The patient digital door display is described in further detail below in relation to FIGS. 2 and 3 and examples of a display are shown in FIGS. 11A and 11B.

The system 100 also includes an automated medical communications board controller device 120. The automated medical communications board controller device communicates with and controls the automated patient digital whiteboard, patient digital door display, and monitoring station digital board using a medical display network 121 (or alternatively the medical facility network 101) to automatically provide content, such as patient and safety information for presentation by the boards without the need for hospital staff interaction.

The automated medical communications board controller device includes at least one processing device, a storage device, and one or more communications interfaces to send and receive data via the various system networks. In one example, the automated medical communications board controller device may be a server running a number of software applications, such as for example, a hospital network application interface, patient device application interface, and medical display application. The automated medical communications board controller device includes a network communications interface for sending and receiving data on the medical facility network. In one example, the server also may include additional network interfaces to send data and receive data on the AMIC network, a VPN network, and/or a private patient device network. The automated medical communications board controller device uses the network connections to automatically communicate with a one of a number or disparate medical facility systems, such as the patient health records system, the patient device system, and a nurse call and badging systems of the medical facility, such as a hospital.

The automated medical communications board controller device is programmed to automatically access patient records and medical information using the medical facility network. In addition, the automated medical communications board controller device receives information regarding patient health devices via the medical facility network or a private third-party patient health device network and the patient device system. The automated medical communications board controller device builds a database of records for each patient location and continually updates and maintains the database. The automated medical communications board controller device accesses the database to automatically monitor and processes patient information associated with the location to generate up-to-date, real time content customized for each type of display, such as, for example, the automated patient digital whiteboard, patient digital door board, and monitoring station digital board.

The automated medical communications board controller device automatically accesses, aggregates, and processes information related to a patient's care from multiple data sources, formats, and network structures without the aid or intervention of medical staff to generate a customized medical communications interface display. Using the database, the system automatically pulls together and culls multiple data sources from different part of the medical facility to detect potentially unsafe conditions that would otherwise go undetected and alert both medical staff and the patients themselves to prevent harm and injury. In addition, the automated medical communications board controller device translates standard medical information types, terms, and jargon into more patient friendly formats to aid a patient in monitoring their own care. Moreover, the content presented to the patient can be translated into a patient's native or preferred language to improve communication with medical staff and improve a patient's overall comfort and wellbeing during their stay at the medical facility. Because the controller automatically accesses, aggregates, and processes information related to a patient's care from multiple data sources, formats, and network structures without the aid or intervention of medical staff it is not susceptible to human errors, such as failing or forgetting to configure a device or setting, or forgetting to enter information or take a required action. In addition, the controller does not require any additional work on the part of the medical facility staff to provide its functionality and benefits.

In addition, the automated medical communications board controller device can be remotely accessed through a VPN over a communications network 160, such as the Internet by one or more remote computers or workstations 165. The automated medical communications board controller device may be secured from unauthorized access by one or more security measures 167, such as a firewall. The VPN may be used to monitor and maintain the automated medical communications board controller device and AMIC network. In addition, the VPN can facilitate the interface template, widget design, and customization for the medical facility.

The automated medical communications board controller device also may access, monitor, and interact with other medical facility systems 180 such as, badging systems, to obtain credentials and/or pictures of medical staff, scheduling systems, such as a nurse call or patient rehabilitation, and other data that may be used to generate the content presented to patients and staff.

System Hardware

Figure 2:
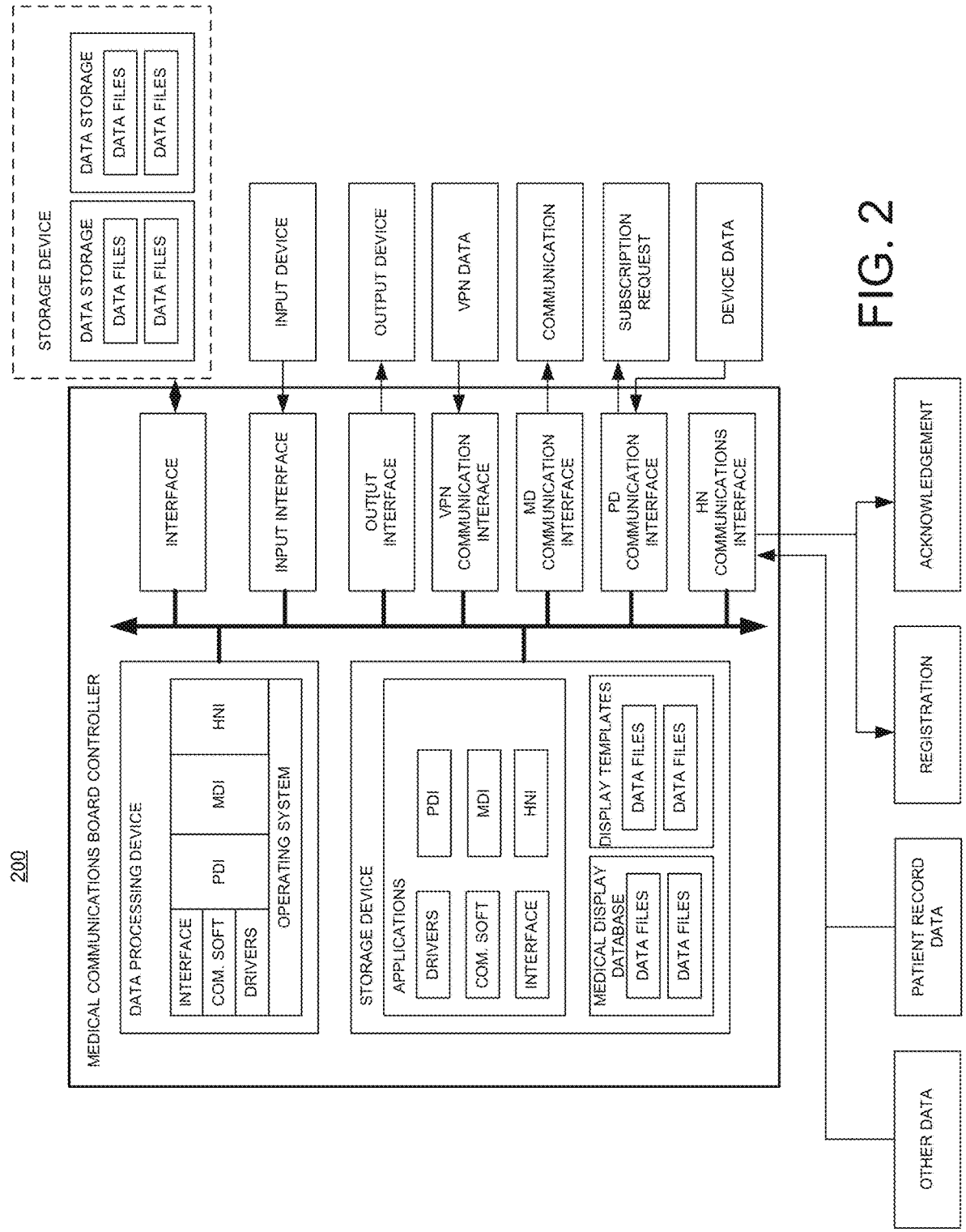
FIG. 2 is a block diagram illustrating an example of a system control device.

FIG. 2 shows a block diagram illustrating an example of a system automated board controller device, such as an automated medical communications board controller device 120. Referring to FIG. 2, one general example 200 of the hardware components of an automated board controller includes at least one data processing device and at least one storage device. The processing device implements various software applications and accesses, parses, assembles, creates, manipulates, and processes data. The applications and data may be stored in an internal storage device and/or an external storage device. The data may be stored in data files or records organized in a data storage, such as a relational database. Specific examples and descriptions of data processing devices and storage devices are provided below.

The automated board controller also may include one or more input interfaces and output interfaces. For example, an input interface provides an input for a user input device (e.g., a touch screen, a keyboard, a key pad, a touch pad, a mouse, a pointer device, a trackball, a joystick, and a microphone, among others). An output interface provides output for an output device (e.g., a display device, such as a touch screen display, a Liquid Crystal Display (LCD), a Light Emitting Diode (LED) display, a speaker, and a printer, among others).

The control device also includes a board network communications interface device and at least one communication/data bus. The board network communications interface device may include one or more network communications interfaces that provide a physical connection to the various system networks to send and receive data on the networks. The communications interfaces may include, for example, a medical facility communications interface, a patient health device network interface, a medical display communications interface, and a VPN communications interface. The communication interfaces allow the processing device to send and/or receive signals in one or more communication formats allowing the apparatus to communicate or exchanged data with other devices, such as TCP/IP transporting data formats, such as, HL7, ODBC, SEWSI, SOAP/WSDL, XML, among others. Example of interfaces include network wired and wireless interface cards for wired Ethernet and 802.11 wireless network connections. The communications bus allows various components of the automated board controller to access and/or exchange data with each other.

The automated board controller also may include one or more associated peripheral devices (not shown). As is appreciated by those skilled in the art, any of these components (other than at least one processing device) may be included or omitted as consistent with the description and teachings herein to create different configurations or types of automated board controllers, for example, to perform specific or specialized needs or tasks, generalized needs or multiuse tasks, or for various performance criteria, such as, speed, cost, efficiency, power consumption, data types, data load, ease of use, among others.

The automated board controller is programmed or configured to implement a number of software applications or processes. For example, the processing device implements an operating system, such as LINUX, OS X, QNX, MICROSOFT WINDOWS and other UNIX and non-UNIX based operating systems. A number of applications run on the operating system such as, various interfaces, communications software, and drivers, in addition to a hospital network application interface, a patient device application interface, and a medical display application. The hospital network application interface, the patient device application interface, and the medical display application work in conjunction with medical communication interface storage structure, such as a medical display database maintained by the automated board controller.

In one example, the medical display database can be implemented in one or more relational databases that store information about both the data and how it is related. The following are examples of data that may be stored in the database: a Patient Nickname, Today's Date, a Nurse Name, Photo and Phone Number, a Nurse Assistant Name, Photo and Phone Number, a Primary Physician Name and Photo, a Care Manager Name and Photo, a Pain Level and corresponding Wong Baker Visual and Optional Pain Trending indication, a Medication, a next Medication Time, a Mobility along with custom visuals, a Fall Risk, a Plan for The Day, a Diet, Allergies, a Potential Discharge, Oxygen, Next Round, Notes, Internal Advertising, Alerts when applicable for bed alarm, side rail, bed height and bed brake violations, a Medication Overdue Alert, a Round Overdue Alert, an Isolation Identifier Including Gowning/Safety Procedures, a Nurse on Duty Including a Nurse Name and Phone Number, a Patient Spoken Language, a Patient Written Language, a Fall Risk Identifier, a Latex Allergy Identifier, a Hearing Impaired Identifier, Vision Impaired Identifier, Palliative Care Identifier, Room Last Cleaned by Including Initials of Cleaner and the Date and Time of Cleaning, a Room Number, an Out of Bed Status (OOB). One will appreciate that this list is exemplary and that other data, types, and associations may be stored.

The data and relationships may be represented in one or more flat, two-dimensional tables that preserve relational structuring. Each table includes a number of rows and columns. Each row may store a data record representing a data set for a single item (e.g., a patient location, such as a hospital room). Each column in the table may store and attribute or field of the data item (e.g., a location ID, a patient ID, medical personnel IDs, a patient health device ID, etc.). Other records may include a medical staff record including attributes of medical personnel IDs, a name, a type (e.g., nurse, doctor, care manager, nurse assistant), a Photo, and a Phone Number. A patient record may include attributes of a patient ID, a name, a medical personnel ID, isolation status, a Pain Level, a pain trend, a Fall Risk, a Plan for The Day, a Diet, Allergies, a Potential Discharge, Oxygen, Next Round, Notes. A patient health device record may include attributes of an ID, patient health device data (e.g., bed alarm armed, a side rail position, a weight, a bed height, and bed brake setting), alarms (e.g., bed not armed, side rail not armed, break not armed, OOB status and other violations). A pain level record may have attributes indicating different pain level and corresponding Wong Baker Visual depictions for each pain level and a trending of the pain level.

Medical board communications interface templates, such as digital board templates also may be created and stored by the automated board controller for each type of medical digital board (e.g., the automated patient digital whiteboard, the patient digital door board, and the monitoring station digital board). Display widgets are chosen by the medical facility to build the content proved by each medical display board and are linked to the applicable data in the medical display database. The widgets chosen allow a completely customizable display interface that may be positioned, changed, updated, and/or rearranged over time. These templates may be designed and maintained remotely (e.g., on workstation 165) and uploaded to the automated board controller for storage by a memory storage device. The automated board controller uses a display template to obtain information from the database to build or assemble the display content for each medical digital board presented in the medical facility that is maintained by the system.

The automated board controller includes software to implement a database management system that includes a standard query language (SQL) that manages the relational database and controls reading, writing, modifying, and processing the information stored in the databases.

The hospital network application interface is implemented by the processing device and runs on the operating system. The hospital network application interface allows the processing device to send and receive data on the medical facility network. In particular, the hospital network application interface allows the automated board controller to communicate with medical facility systems, including the patient health records system to automatically receive patient data. The hospital network application interface allows the automated board controller to be "back-end" agnostic allowing the automated board controller to connect to any one of a number of different EHRs, such as, for example, MEDITECH, CERNER, EPIC or any other HL7, SQL, MYSQL, ORACLE or ODBC compliant data source.

In one implementation, the automated board controller implements an HL7 communications standard interface to query the EHR system for patient data. The hospital network application interface sets up a communications protocol with the patient health records system, such that each time a patient is admitted to the hospital (or to a location in the hospital where displays are used) the patient health records system sends patient information to the hospital network application interface. For example, the hospital network application interface may receive an HL7 Admit Discharge Transfer (ADT) message providing information about a patient. The patient information may include a name, a primary physician, an isolation status, a Pain Level, a pain trend, a Fall Risk, a Plan for The Day, a Diet, Allergies, a Potential Discharge, Oxygen, Next Round, patient charts, test result, and other medical notes and information. In addition, any time data for a patient change, the updated information may be sent from the patient health records system to the hospital network application interface.

In one example, the hospital network application interface may specify the type of updated information that is sent by the patient health records system. In another embodiment, the patient health records system may push specific data or all patient data to the hospital network application interface. In this case, the hospital network application interface processes the data to determine any relevant data needed by the hospital network application interface. In yet another embodiment, the hospital network application interface may monitor the periodic backup of data by the patient health records system to process the backup data to determine any relevant data needed by the hospital network application interface.

The obtained patient data is then written by the hospital network application interface to the medical display database in the appropriate record. Patient data records may be secured and managed to comply with HIPPA requirements. One example of a process implemented by the hospital network application interface is provided below in relation to the description of FIG. 5. In one example, when new or updated data written to the medical display database and flag or other indication may be set to aid the medical display application in determining data that is new or updated.

The patient device application interface subscribes to patient health devices managed by a corresponding patient device system in locations that have installed AMICs. For example, the patient device application interface subscribes to a patient device system that is connected to and manages a number of patient health devices. In one example, the patient device application interface sends a message to a patient device system to identify locations of interest (e.g., a patient room number). The patient device system determines whether a patient health device is associated with the location. For each patient device associated with a location of interest, the patient device application interface maintains a subscription for that device. The subscription includes a patient device identifier and information that should be reported by the patient device system to the patient device application interface. For example, the patient device application interface may enter in a subscription for a patient bed, the patient device application interface provides a bed identifier and data that it wishes to monitor, such as whether a bed alarm is armed, side rail positions, a weight, a bed height, a Fowler setting, and bed brake setting. Whenever, the patient device system determines a change in any one of the monitored data for a subscribed bed ID, the patient device system sends a message via the medical facility network or the private network addressed to the patient device application interface with the data requested for the subscription.

Data may be exchanged via the medical facility network or a private patient device network. A TCP/IP data format may be used. In addition, the patient device application interface can be programmed to communicate or provide an interface with any third-party proprietary information protocol (e.g., the SEWSI protocol for STRYKER medical devices).

The patient device application interface receives the message data, determines a corresponding patient, and accesses the corresponding patient data from the medical display database. The patient device application interface then processes the message data using the accessed patient data to determine if safety or any other conditions have been met and whether any alerts should be generated. The patient device application interface then writes information to the medical display database, such as any generated alerts. One example of a process implemented by the patient device application interface is provided below in relation to the description of FIG. 6.

In one example, as mentioned above, the patient device application interface implements an automated safety feature. For example, when the patient device application interface receives information for a patient health device indicating a change, the patient device application interface accesses the medical display database and determines a patient and patient information that corresponds to the patient health device. The patient device application interface processes the information received from the patient device system and the information retrieved from the medical display database to determine whether there is potential risk or safety issue for the patient. For example, the patient device application interface can determine whether a patient health device reading or data is within an acceptable range, limit, tolerance, or setting based on the patient's medical information, which was automatically obtained from the patient health records system. If data from the patient health device is unacceptable for the patient, the patient device application interface can generate appropriate alarms or indications which are used by the by the medical display application to present the alarms or indication as information on an appropriate display board.

In one example, the patient health device may provide data to the patient device application interface in the form of a weight. The patient device application interface processes the weight information to determine that the weight indicates a patient is not in their bed. The patient device application interface accesses the medical display database and determines the patient corresponding to the bed and determines whether there are restrictions on the patient's movement. If the patient, for example, is a high fall risk, the patient device application interface can generate a message that an OOB alarm should be displayed on the patient's automated patient digital whiteboard, the patient digital door board, and on the corresponding monitoring station digital board. If the patient is not a high fall risk, the patient device application interface can generate a message that the patient's status on the monitoring station digital board should be updated to indicate OOB status. One example of such an automated bed safety process implemented by the patient device application interface is provided below in relation to the description of FIG. 7. Other indications can also be provided, such as the failure to set an exit alarm on the bed. In another example, if a nurse forgets to set the exit alarm for a bed, the automated board controller is able to ascertain the patient is a high fall risk from the patient record in the medical display database, receive a message from the patient bed indicating the exit alarm is not armed, determine the exit alarm should be armed for a high fall risk patient, and display an appropriate alert on a medical display. As a result, potential unsafe conditions are automatically identified by the automated board controller without input from the medical staff. In addition, errors or omissions of protocol by the staff can be automatically identified by the automated board controller to alert both the staff and patient (or family/friends) so that the problem is identified and corrected (as opposed to ongoing without anyone's knowledge) before any serious consequences or injury occurs to the patient.

In addition, the system can display alerts generated by devices. For example, if the exit alarm on the bed is set and the patient triggers the alarm by leaving the bed, the patient device application interface can detect the alarm condition and board controller can generate a display alarm condition on the patient digital whiteboard, the patient digital door board, and the monitoring station digital board. This is useful because many traditional nurse call systems, which are designed to handle dispatch of the bed exit alarm, do not specify the location in which the alarm is sounding. As a result, the staff must follow the sound and look for a light outside of the offending room to determine the patient location in question. Additionally, the traditional nurse call system requires a 37-pin connector to be plugged into the bed in order for it to monitor the bed exit alarm. These cables are commonly forgotten by staff and left unplugged. In addition, this cable is composed of 37 small pins that are easily and commonly bent, pulled out and generally fragile making them unreliable. The patient device application interface generates an alert on the monitoring station board, which clearly defines where the alarm is coming from by patient name and/or room number and is not dependent on the connection of the nurse call connector or proper function. Lastly, even in the event that the nurse call system provides location functionality and is operating correctly, the patient device application interface generation of an alarm indication provides a backup to these systems in case of some other malfunction. For example, if the nurse call system encounters an error or simply goes down for routine maintenance, the patient device application interface can generate an alert in its place.

The processing device implements the medical display application to interface with the medical display database to create the display data for each of the automated patient digital whiteboards, patient digital door boards, and monitoring station digital boards. The medical display application instructs the processing device to search the medical display database for information that has changed, been updated, and/or is newly created in the medical display database. The medical display database is configured to allow the processing device to determine whether new or updated information is present in the medical display database. When new or updated information is detected, the information is processed to determine which displays are affected by the new or updated information.

The medical display application also instructs the processing device to access a display template for the corresponding determined display. The display templates are stored by the storage device associated with the automated board controller for each type of medical display (e.g., the automated patient digital whiteboard, the patient digital door board, and the monitoring station digital board). The automated board controller determines which display widgets correspond to the determined display and/or data type of the new or updated information. In one example, the automated board controller uses the template to build an entire display by accessing the data from the medical display database corresponding to each of the widgets in a display template to render an entire display. In this case, the medical display application instructs the processing device to render a complete display in a corresponding format. The completely rendered display is then packaged and addressed to a specific display corresponding to the new or updated information. In another example, only widgets that correspond to updated information are assembled. In this instance, the assembled one or more widgets corresponding to the updated or new information are packaged, addressed to a specific display, and transmitted to the display on the automated display network. In this example, the display control device processes, disassembles, and renders the widgets associated display device.

One example of a process implemented by the medical display application is provided below in relation to the description of FIG. 8.

The automated board controller may have an associated external device storage or backup storage device that stores a copy of the medical display database and templates.

Figure 3:
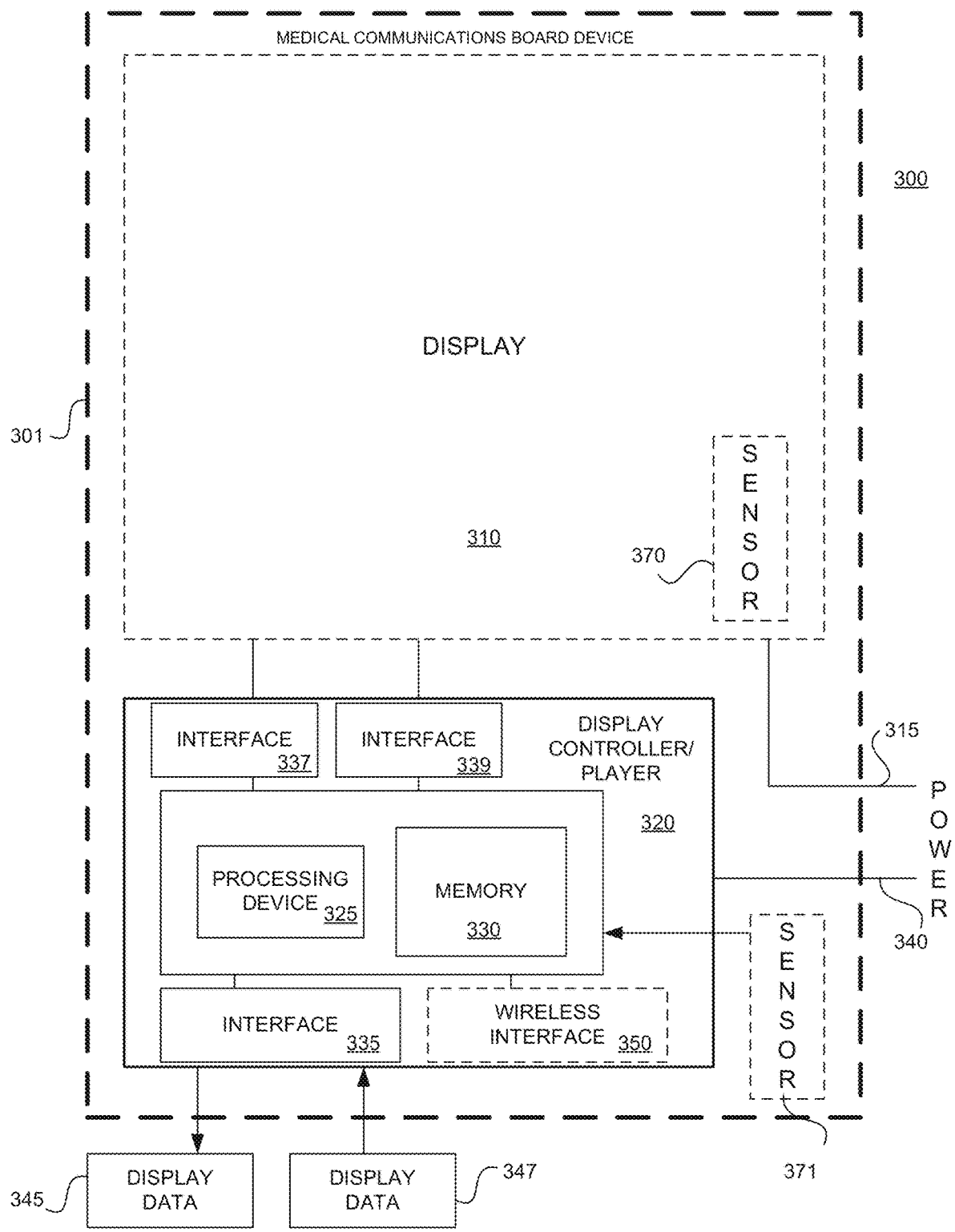
FIG. 3 is a block diagram illustrating an example of a digital whiteboard for use with the system FIG. 1.

FIG. 3 shows a block diagram illustrating an example 300 of a medical communications board device for use with the system FIG. 1. The medical communications board device may be used to implement any one of the automated patient digital whiteboard, the patient digital door board, and the monitoring station digital board. The medical communications board device includes a housing/enclosure 301, a display 310, and a medical board control device or display controller 320.

As shown in FIG. 3, the medical communications board device includes a housing 301 and/or enclosure to secure the various components of the medical communications board device. The housing may be made of any durable material and provide customized finishes that suit or match a décor of the medical facility. The housing may be removable or otherwise provide access to various system components. The housing also may include holes, slots, or other openings for ventilation of the components. The housing may include hardware (not shown) for mounting on various locations, such as walls of the medical facility. The hardware may be adjustable to provide different viewing angles suitable for the location the medical communications board device.

The medical communications board device includes a digital display 310. In one example, the display is a backlit color Liquid Chrystal Display (LCD) that includes one or more inputs, such as a video input (e.g., HDMI, DVI, VGA input) and a serial input (e.g., USB or RS-232 input). In other embodiments, the display may be implemented using LED display and OLED display, or combined LED and LCD technologies may be used, such as, for example, LED backlit LCDs. The display may be sized according to the type of display or environment in which it is used. The digital display also includes a power connection 315.

The medical communications board device also includes a display controller device 320. For example, the display controller device may be implemented using a solid-state device that includes a processing device and/or graphics processor 325, memory device 330, a medical board communications network interface, such as network interface 335, a video interface 337, a serial interface 339, and a power connection 340.

The network interface 335 connects to the display network (or optionally the medical facility or other network) to receive communication packages 345 from the automated board controller (e.g., display information) and send communication packages 347 to the automated board controller (e.g., acknowledgements). In one example, the network interface is an Ethernet interface receiving and sending data packages using the TCP/IP protocol.

The video interface provides video signals to the display for presentation to a viewer. The video interface may be a DVI, a VGA, or a HDMI interface.

The serial interface may be used to send control signals and other data signals to the display device. In one example, the serial interface is a RS-232 or USB interface.

The display controller's communications network interface also may include an optional wireless interface 350 for communication with the automated board controller via a wireless network.

The processing device implements an operating system and several applications or software components which run on the operating system. One application is a display application interface that implements a display process. In one example, the display application may implement the process shown in FIG. 9 and described in further detail below.

The display processing device monitors the display network for messages received by the communications interface that are addressed to the display controller. When a message is received that is addressed to the display control device, the display processing device unpacks and stores the payload of the message. The display processing device validates the content of the payload, and sends an appropriate acknowledgement to the automated board controller via the communications interface (e.g., an error message for invalid or corrupted content). If the content is valid, the display processing device renders the content for presentation by the display device and outputs the content for presentation using the video interface. In one example, the display controller device may be implemented using a NOVENTRI SF-200 Signage Player.

The medical communications board device 310 may include an optional ambient light sensor 370. The ambient light sensor can detect illumination, such as light sources in the patient's room. The sensor and display may be programmed to select an appropriate brightness based on the amount of light detected. In one example, the sensor may provide an auto-dimming feature that adjusts the medical display to a minimal brightness setting when the patient is asleep (e.g., when light sources in the room are minimal or dimmed). Alternatively, an optional ambient light sensor 371 may be connected to a port of the display controller. The processing device of the controller reads a detected amount of illumination provided from sensor. The processing device determines a corresponding brightness based on the amount of light detected from a lookup table and generates a signal to control the brightness of the display using a serial connection to the display, such as the RS-232 connection. In one example, the processing device of the display controller may provide an auto dimming feature that adjusts the medical display to a minimal brightness setting when the patient is asleep (e.g., when light sources in the room are minimal or dimmed).

Patient Device System

Figure 4:
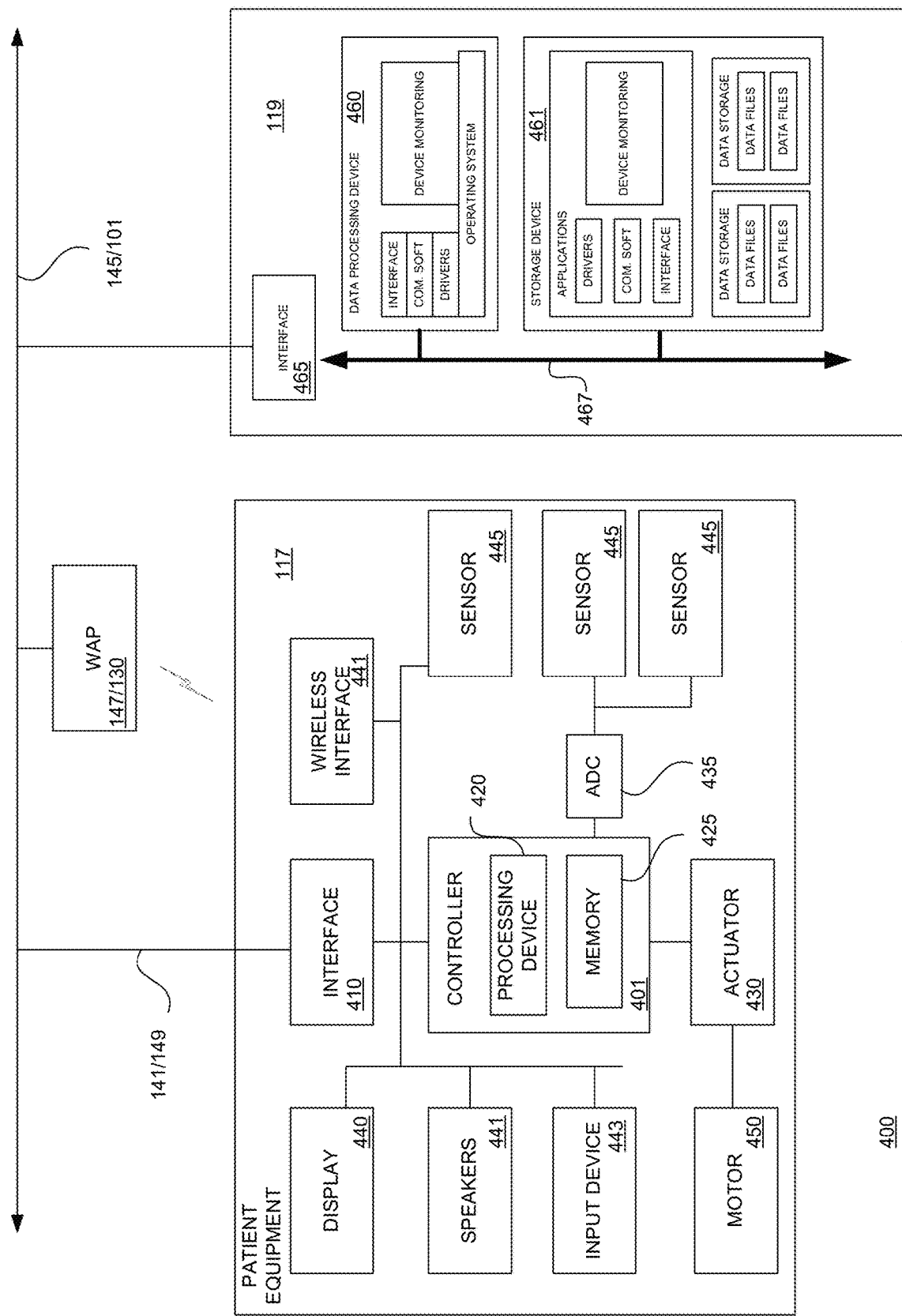
FIG. 4 is a block diagram illustrating an example of a patient device system for use with the system of FIG. 1.

FIG. 4 shows a block diagram illustrating an example of a patient device system 400 for use with the system of FIG. 1. As shown the system 400 includes a communications network 101, 145, a wireless access point 130, 147, a patient health device 117 with connection 141, 149, and a patient device system 119. A single patient health device and patient device system are shown for illustrative purposes; however, one skilled in the art will appreciate that multiple patient health devices and patient device systems may be used for any particular application based on the number of patient locations and arrangement of patient locations in within a medical facility.

The patient health device includes a controller 401, a communications interface 410, a wireless communications interface 411, and a communications bus 415. The controller includes a processing device 420 and a memory device 425 connected to the communication bus, in addition to a number of ports for connection to other devices, such as an actuator 430 and an analog to digital converter (ADC) 435. The patient health device also may include a display (e.g., a touch screen display, a Liquid Crystal Display (LCD), a Light Emitting Diode (LED) display) 440, one or more speakers 441, an input device (e.g., a touch screen, a keyboard, a key pad, a touch pad, a mouse, a pointer device, a trackball, a joystick, and a microphone, among others) 443, and one or more sensors 445 (e.g., digital sensors or analog sensors).

The communications interfaces provide a physical connection to the various system networks to send and receive data on the networks. The communications interfaces may include, for example, a medical facility communications interface or a patient health device network interface. The communication interfaces allow the controller processing device to send and/or receive signals in one or more communication formats and/or protocols, such as SEWSI using TCP/IP. Examples of interfaces include network, wired and wireless interface cards for wired Ethernet, and 802.11 wireless network connections. The communications bus allows various components of the patient health device to access and/or exchange data with each other.

In the example, shown in FIG. 4 an ADC connects two analog sensors to the controller. A third digital sensor is connected to the controller via the communications bus. For example, the analog sensors may detect the position of a bed guardrail, the engagement of a bed brake, or the weight of a patient in the bed. The digital sensor may measure the bed height. Information from the sensors is provided to the control device. Other sensors may be used, such as, for example, a bed angle sensor, a nurse bell sensor, and a patient rotation assist sensor.

The actuator is connected to a motor 450. For example, the motor may be an electrical/mechanical motor that adjusts the height of a patient bed. The actuator controls the motor. In one example, the actuator may control the motor to adjust the height and/or angle of a patient's bed.

The controller processing device processes the sensor information, such as encoding the sensor information, saving the information, and packaging the sensor and other information for transmission to the PHS via the network 101, 145. The controller processing device also receives information addressed to the controller via the network from the patient health device. The controller processing device processes and stores the received information. For example, the information may cause the controller to adjust bed height, enable an exit alarm, read a sensor, and/or report a reading. The controller processing device also outputs control signals to the actuator to control the motor.

The patient health device shown in FIG. 4 is exemplary. In one example, the patient health device may be a patient bed, an infusion pump or medication dispensing apparatus, or a patient monitoring apparatus; however, or other devices with components similar to those examples given above used in association with care of a patient. As is appreciated by those skilled in the art, the numbers and types of components may be included or omitted consistent with the teaching herein to create different configurations or types of patient health devices, for example, to perform specific or specialized needs or tasks, generalized needs or multiuse tasks, or for various performance criteria, such as, speed, cost, efficiency, power consumption, data types, data load, ease of use, among others.

FIG. 4 also shows includes a patient device system. The patient device system includes at least one data processing device 460 and at least one storage device 461. The processing device implements various software applications and accesses, creates, manipulates, and processes data. The applications and data may be stored in an internal storage device and/or an external storage device. The data may be stored in data files or records organized in a data storage.

The patient device system also includes one or more communications interfaces 465 and at least one communication/data bus 467. The communications interfaces provide a physical connection to the various system networks to send and receive data on the networks. The communications interfaces may include, for example, a medical facility communications interface and a patient health device network interface. The communication interfaces allow the processing device to send and/or receive signals in one or more communication formats allowing the apparatus to communicate or exchanged data with other devices, such as the patient health device and the automated board controller. Data may be communicated using the TCP/IP protocol in a SEWSI format, among others. Examples of interfaces include network, wired and wireless interface cards for wired ETHERNET, and 802.11 wireless network connections. The communications bus allows various components of the patient device system to access and/or exchange data with each other.

The patient device system is programmed or configured to implement a number of software applications. For example, the processing device implements an operating system. A number of applications run on the operating system such as, various interfaces, communications software, and drivers, in addition to a patient health device management application. For example, the management application allows the automated board controller to subscribe to individual patient health devices managed by the patient device system in locations that have installed automated medical displays. In one example, the patient device system receives a message from an automated board controller to identify locations of interest (e.g., a patient room number). The patient device system determines whether a patient health device is associated with the location. For each patient device associated with a location of interest, the patient device system maintains a subscription for that device. The subscription includes a patient device identifier and information that should be reported by the patient device system to the automated board controller. For example, the patient device system administers a subscription for a patient bed and reports any changes in data received from patient health device data corresponding to the subscription, such as whether a bed alarm is armed, side rail positions, a weight, a bed height, a Fowler setting, and bed brake setting. Whenever, the patient device system determines a change in any one of the monitored data for a subscribed bed ID, the patient device system sends a message via the medical facility network or the private network addressed to the automated board controller with the data requested for the subscription.

Data may be exchanged via the medical facility network or a private patient device network. A TCP/IP data format may be used. In addition, the patient device system may be programmed to communicate using a third-party propriety information protocol (e.g., the SEWSI protocol for STRYKER medical devices).

System Processes

Figure 5:
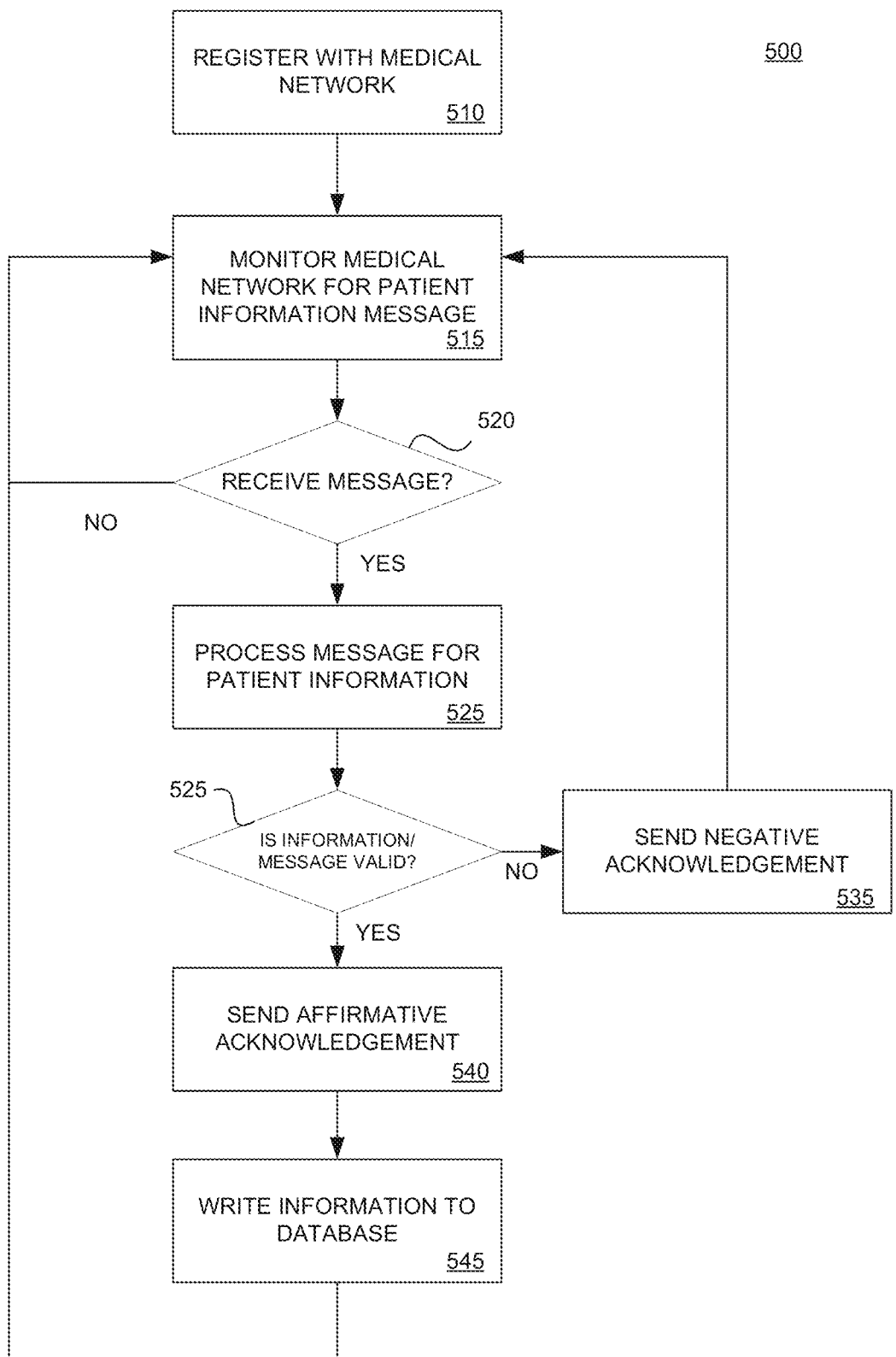
FIG. 5 is a flow chart illustrating an example of a medical network interface process.

FIG. 5 shows a flowchart illustrating an example 500 of a medical network interface process. The process is implemented by the automated board controller. In one example, the process may be implemented as part of the hospital network application interface.

In operation 510, the automated board controller registers with the medical network. For example, the automated board controller may exchange data with the patient electronic records system to establish authentication and communication parameters used by the systems.

In operation 515, the automated board controller monitors the medical network for patient information. For example, the automated board controller can monitor the network for ADT messages from the patient electronic records system addressed to the automated board controller. In another example, the automated board controller may "actively" monitor the patient electronic records system for changes or for backing up of data to access patient information.

In operation 520, the automated board controller determines whether a message is received from the medical network. If the automated board controller actively monitors the patient electronic records system this step may be omitted or changed to detect when updated patient data is available.

If message is received, in operation 525 the automated board controller processes the message for patient information; otherwise, the automated board controller continues to monitor the medical network for patient information.

In operation 530, the automated board controller determines whether the message is valid. If the message is not valid, in operation 535 the automated board controller sends a negative acknowledgement message to medical network. If the message is valid, in operation 540 the automated board controller sends an affirmative acknowledgement message to medical network. If a negative acknowledgement is sent, the patient electronic records system can resend the information in response.

In operation 545, the received information is written to the appropriate records in the medical display database. In addition, a flag may be set for each new record, or for records that have newly written, changed, or updated information. After writing the information to the medical display database, the automated board controller continues to monitor the medical network for additional information.

Figure 6:
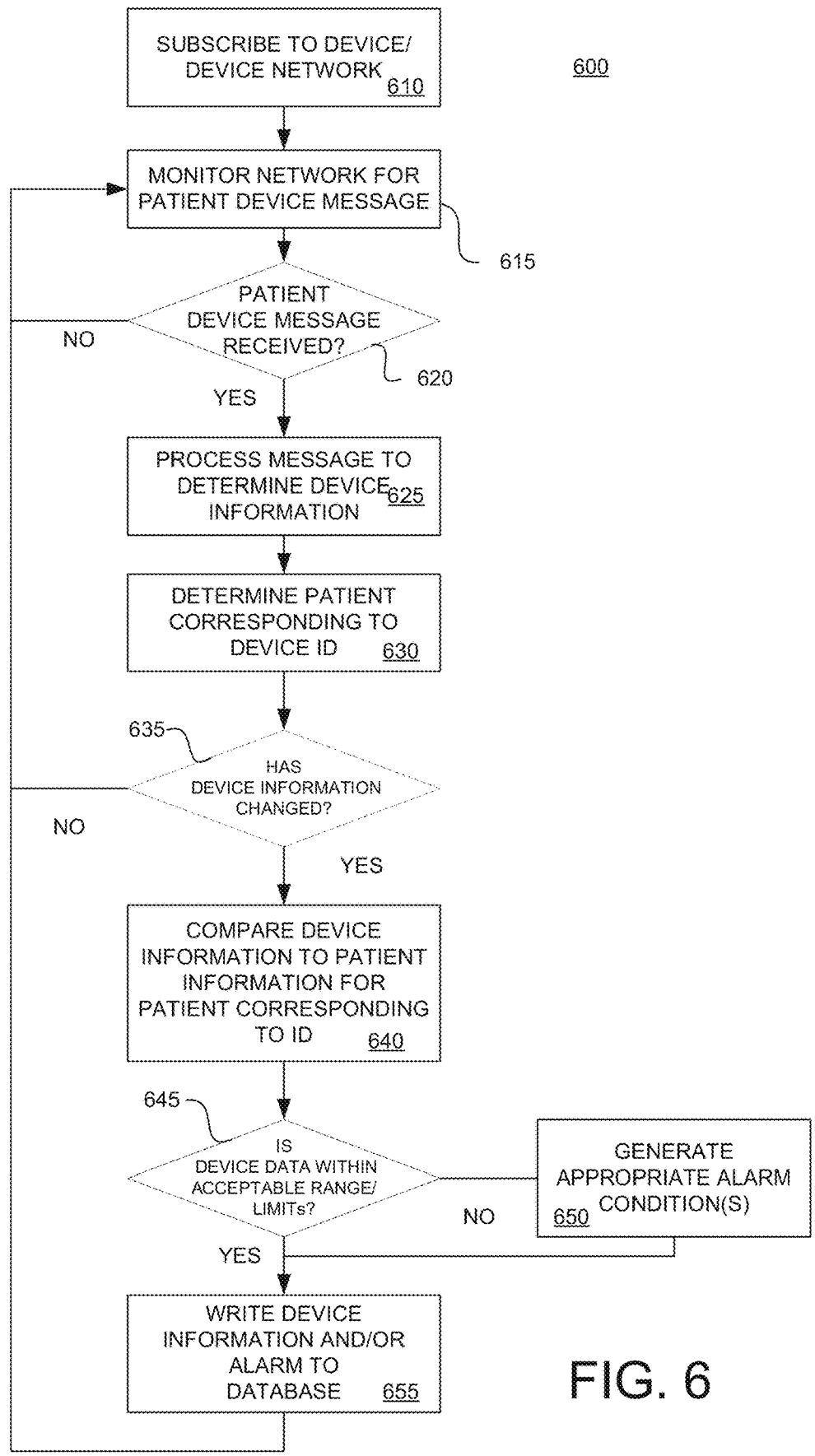
FIG. 6 is a flow chart illustrating an example of a patient device interface process.

FIG. 6 shows a flowchart illustrating an example of a patient device interface process 600. The process is implemented by the automated board controller. In one example, the process may be implemented as part of the patient device application interface.

In operation 610, the automated board controller subscribes to the patient device network system or a patient device on the device network. For example, the automated board controller can provide a device ID that it wishes to receive updates from the device related thereto. In another example, the automated board controller can provide room locations to the patient device system, which then determines device IDs corresponding to the room locations provided by the automated board controller.

In operation 615, the automated board controller monitors the device network for patient device messages. Message may be addressed to the automated board controller corresponding to the subscription. The messages may originate from a patient device or a patient device system controlling the patient device.

In operation 620, the automated board controller determines whether a patient device message is received. If a message is received, in operation 625 the automated board controller processes the message to determine the device information; otherwise, the automated board controller continues to monitor the device network for patient device messages. For example, the automated board controller may process the message to determine a patient device ID corresponding to the message or to specific data in the message associated with a patient device ID.

In operation 630, the automated board controller determines a patient corresponding to the patient device ID received in the message. For example, the automated board controller may access the medical display database to search and retrieve information, such as a location corresponding to the patient device ID and a patient ID corresponding to the location. In addition, previous data stored in association with the device ID may be accessed.

In operation 635, the automated board controller determines whether the information received in the message indicates a change in data from the previous patient data. If there has been no change, the automated board controller continues to monitor the network for patient device messages. If there is change, in operation 640, the automated board controller compares the device information to the patient information corresponding to the ID. For example, the device information may indicate an exit alarm is not armed and the patient information may indicate the patient is a high fall risk.

In operation 645, the automated board controller determines whether the device data is within an acceptable range, limit, or otherwise is within parameters assigned for the patient. Using the preceding example, the automated board controller determines for high fall risk patients the bed exit alarm should be set. In this example, the exit alarm is not set and the patient device is determined not to be within acceptable parameters.

If the automated board controller determines that the device data is not acceptable, in operation 650 an appropriate or corresponding alarm condition is registered. For example, a bed exit alarm alert may be generated.

In operation 655, the automated board controller writes the device information and any alarm conditions to the medical display database, and the automated board controller continues to monitor the device network for patient device messages. In addition, information such as flag may be set to indicate a change to the database information.

Figure 7:
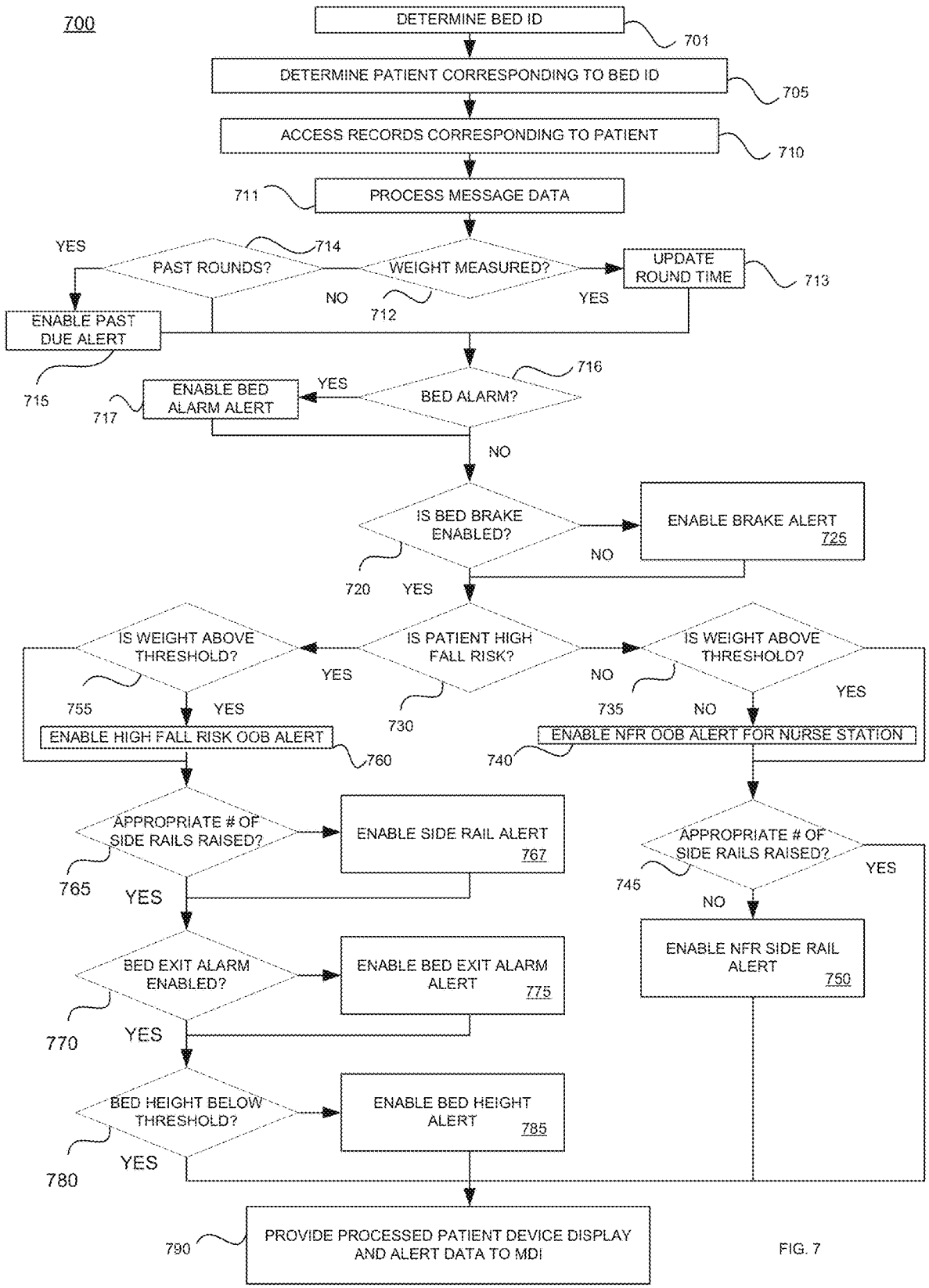
FIG. 7 is a flow chart illustrating an example of a patient device safety process.

FIG. 7 shows a flowchart illustrating an example of a patient device safety process. In this example, the process is implemented as part of the patient device application interface by the automated board controller for an automated patient bed system. However, one skilled in the art will appreciate that other safety processes can be performed for other medical patient devices and/or parameters. For example, an infusion pump with parameters, such as rate of infusion, medication type, whether all medicine has been dispensed, may be monitored.

In operation 701, the automated board controller determines a bed ID. For example, the automated board controller can access a bed ID from the medical display database or a subscription message received from the patient device system.

In operation 705, the automated board controller determines a patient corresponding to the bed ID. For example, the automated board controller accesses the medical display database to determine location ID corresponding to the bed ID and a patient ID that corresponds to the location ID (e.g., a patient room number).

In operation 710, the automated board controller accesses medical records corresponding to the patient. For example, the medical display database for records corresponding to the patient ID.

In operation 711, the automated board controller processes message data received from the patient device system for the bed ID. For example, the automated board controller unpacks data received in the message corresponding to sensor readings for the patient device.

In operation 712, the automated board controller determines whether medical staff has interacted with the patient device. For example, in the case of a patient bed, a nurse may push an input of the bed to determine the patient's weight as part of her rounds. Other examples may include dispensing a medication. If the medical staff interacts with the patient device, in operation 713, the automated board controller determines and saves an update round time for the patient. A round time for the patient may be a time by which or at which the medical staff is supposed to check on the patient and/or otherwise care for the patient, such as take the patient to the bathroom, clean or administer wound care to the patient, remove items from the room, administer one or more procedures, diagnostics, tests, or dispense medication to name but a few. In one example, the automated board controller may determine a time of the last round or a current time, add a predetermined amount of time to save the newly determined time as the next round time for the patient.

In operation 714, if there was no interaction with the patient device, the automated board controller determines whether the current time is past the next round time for the patient. If the current time is past the next round time for the patient, in operation 715, the automated board controller enables a past due round time alert.

In operation 716, the automated board controller determined if there is an alarm for the patient the device. For example, the automated board controller may determine if the bed alarm has been triggered. Other examples, may include disconnecting of equipment alarm, an out of range condition alarm for a monitored patient condition, or an equipment malfunction condition. If there is an alarm for the patient device, in operation 717, the automated board controller can enable an alert for the condition, for example, a bed alarm alert.

In operation 720, the automated board controller determines whether the bed brake is enabled.

If the bed brake is not enabled, in operation 725 the automated board controller sets a brake alert parameter indicating the brake has not been set.

In operation 730, the automated board controller determines whether the patient is allowed to exit their bed. For example, the automated board controller processes the patient information to determine whether the patient is a high fall risk.

If the patient is allowed to exit, in operation 735, the automated board controller determines whether the weight measurement received from the patient device system is above a threshold. For example, the automated board controller determines whether the weight reading from the bed is greater than a predetermined amount, such as, for example, ten pounds. If the weight is not above the threshold, in operation 740 the automated board controller enables an allowed OOB alert. In operation 745, the automated board controller determines whether the side rail data received from the patient device system corresponds to the appropriate number of raised side rails (e.g., for a non-fall risk patient), if not in operation 750, the automated board controller enables a side rail alert.

If the patient is not allowed out of bed (e.g., a high fall risk patient), in operation 755, the automated board controller determines whether the weight measurement received from the patient device system is above a threshold. If the weight is not above the threshold, in operation 760 the automated board controller enables the not allowed OOB alert. In operation 765, the automated board controller determines whether the side rail data received from the patient device system corresponds to the appropriate number of raised side rails (e.g., for a high-fall risk patient), if not in operation 767, the automated board controller enables a side rail alert. In operation 770, the automated board controller determines if the bed exit alarm has been enabled. If not, in operation 775, the automated board controller enables the bed exit alarm alert. In operation 780, the automated board controller determines if the bed height received from the patient device system is below a threshold. If not, in operation 785, the automated board controller enables the bed height alert.

In operation 790, automated board controller writes the processed patient health device display and alert data to the medical display database.

Other types of conditions also may be monitored and alerts created based on the type of medical device monitored. For example, a bed may also be monitored for a Fowler position when a patient that is intubated and an alert provided if the Fowler position is not correctly provided to the patient.

Figure 8:
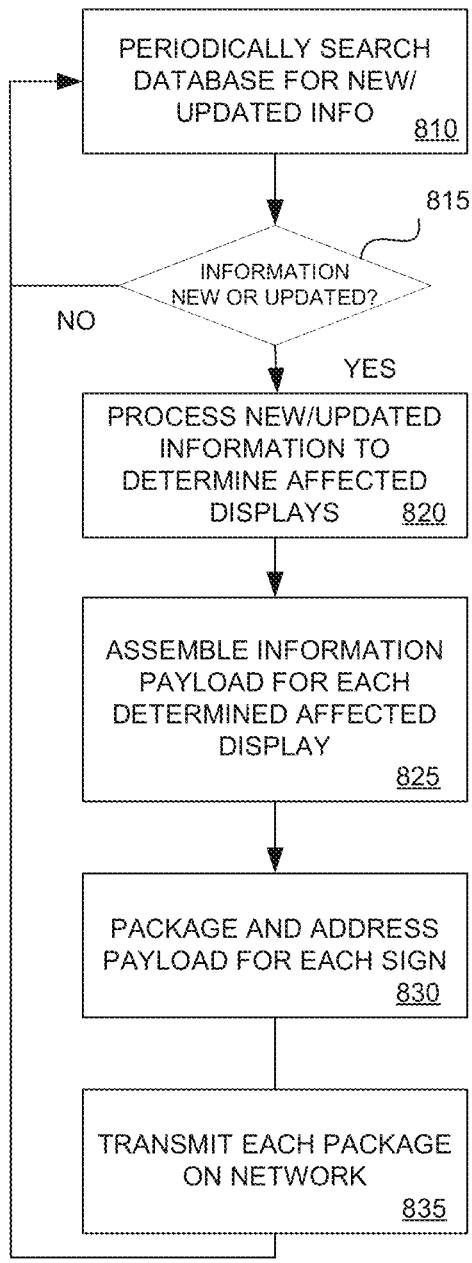
FIG. 8 is flow chart illustrating of a medical display interface process.

FIG. 8 shows a flowchart illustrating an example of a medical display interface process 800. The process is implemented by the automated board controller. In one example, the process may be implemented as part of the medical display application.

As shown in FIG. 8, in operation 810, the automated board controller periodically searches the medical display database for information that has changed, been updated, and/or newly created in the medical display database. For example, the automated board controller may determine if any update flags have been set in the database.

In operation 815, the automated board controller determines whether new or updated information is present in the medical display database, and if not continues to periodically search for new and/or updated information.

If new or updated information exists, in operation 820, the automated board controller processes the new or updated information to determine which displays are affected by the information. For example, an OOB alert would require updating of the monitoring station digital display.

In operation 825, the automated board controller accesses the medical display database and assembles an information payload for each of the affected displays. For example, the automated board controller accesses a display template for the corresponding medical display. In the example above, the medical display is the monitoring station digital display template. The automated board controller determines which display widgets are included in the display template. For each determined display widget, the automated board controller determines and accesses a corresponding data record in the medical display database to obtain the desired data. The display is then assembled by rendering the data according to the display widget. In an alternative method, only the display information that is updated is accessed and the corresponding display widget and data are assembled. In this case, the display is not rendered but sent to the medical display controller for rendering.

In operation 830, the automated board controller packages and addresses each payload to a corresponding display. For example, the rendered display or display widget and data are placed in TCP/IP packets addressed to the display controller corresponding to a location of the medical display associate with the new/updated information.

In operation 835, the automated board controller transmits each package to the display network.

Figure 9:
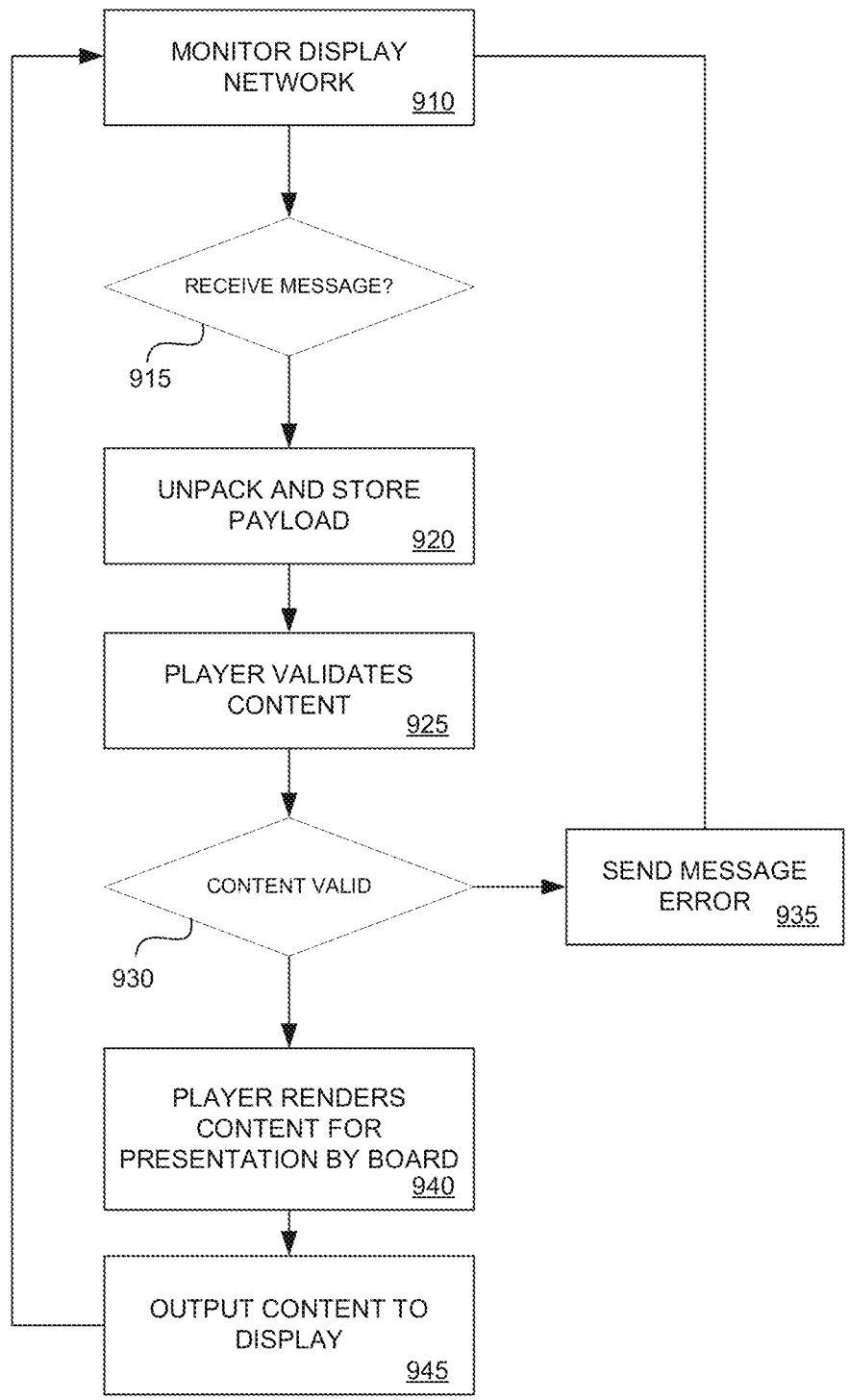
FIG. 9 is a flow chart illustrating an example of medical display process.

FIG. 9 shows a flowchart illustrating an example of a medical display process 900.

In operation 910, the display controller monitors the communications network for messages.

In operation 915, the display controller determines whether a message is received addressed to the medical communications board device. If not, the display controller continues to monitor the communications network for messages.

If a message is received that is addressed to the display controller, in operation 920, the display controller unpacks and stores the payload.

In operation 925, the display controller validates the content, and in operation 930 determines whether the content is valid.

If the content is not valid, in operation 935 the display controller sends an error message on the network to the display controller.

If the content is valid, in operation 940 the display controller renders the content for presentation by the display, or if the content is already rendered, outputs the rendered display.

In operation 945, the display controller outputs the content to the display of the medical communications board device.

Medical Board Communication Interface Examples

FIGS. 10A and 10B, 10C, and 10D show examples of display content for an automated patient digital whiteboard.

Figure 10A:
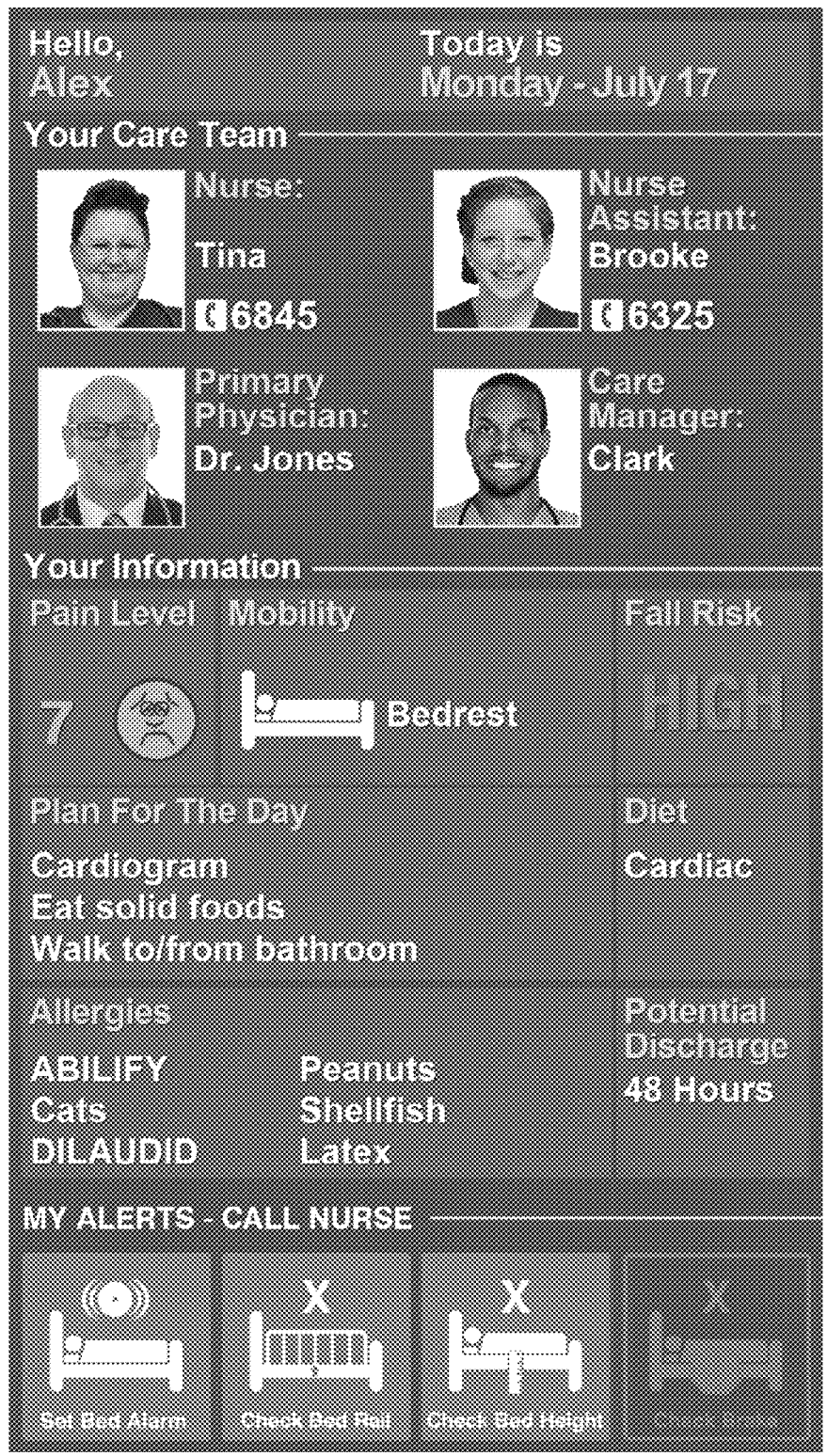
FIGS. 10A, 10B, 10C, and 10D are examples of an interior patient digital whiteboard interface.
Figure 10B:
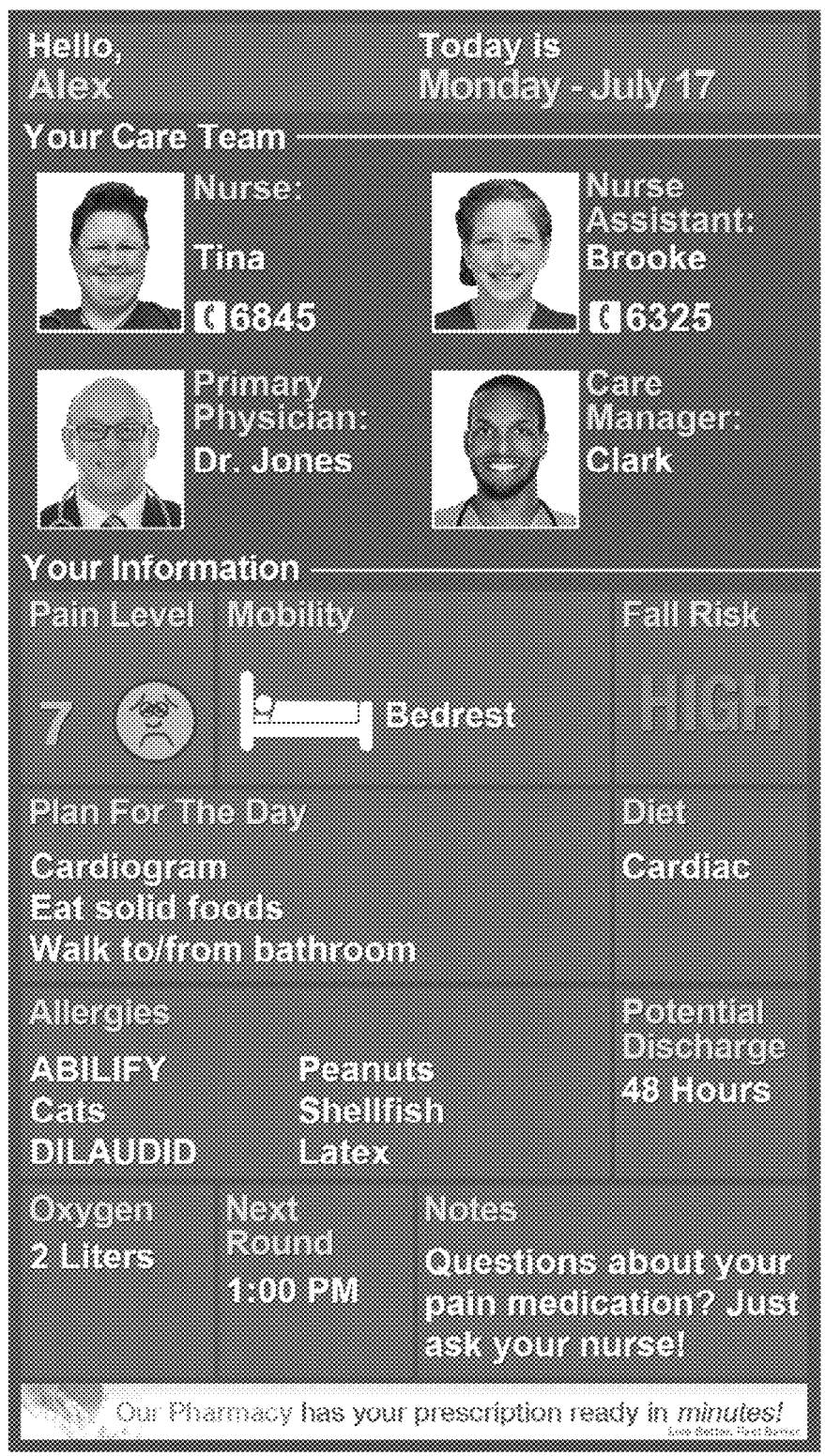

As shown in FIGS. 10A and 10B, the medical display includes a welcome portion, a care team portion, and a patient information portion. FIG. 10A also includes an alert portion.

The welcome portion includes a patient name, a day and a date.

The care team portion includes information about the caregivers. For example, the display provides the patient's assigned nurse, nurse assistant, primary physician, and care manager. The display includes the name and picture for each team member. In addition, call extensions are provided for the nurse and nurse assistant.

The patient information portion includes a pain level, a mobility, a fall risk, a plan for the day, a diet, patient allergies, potential discharge, oxygen, a next round, and notes. The information presented here can be translated from EHR and medical terms to more patient friendly terms or signs. For example, a depicted expression can be provided along with pain level to help patient understanding and an intuitive bed symbol can be used to communicate a bedrest patient.

As shown in FIG. 10A, an alert portion display safety alerts automatically determined by the automated board controller that are relevant to the patient. For example, alerts are provided for bed alarm, bed rail, bed height, and bed brake. In this example, the bed alarm has not been set, the bed rail is not properly positioned, and the bed height needs to be adjusted. FIG. 10B shows an example of the display after the safety alert conditions have been satisfied.

In addition, information can be translated into a preferred language to help facilitate patient understanding and communication. As a result, of the information provided by the medical sign in the patient's room, the patient, family, and/or friends are able to better monitor and understand the patient's care and are able to point out errors or inconsistencies to the care team and medical personnel.

Figure 10C:
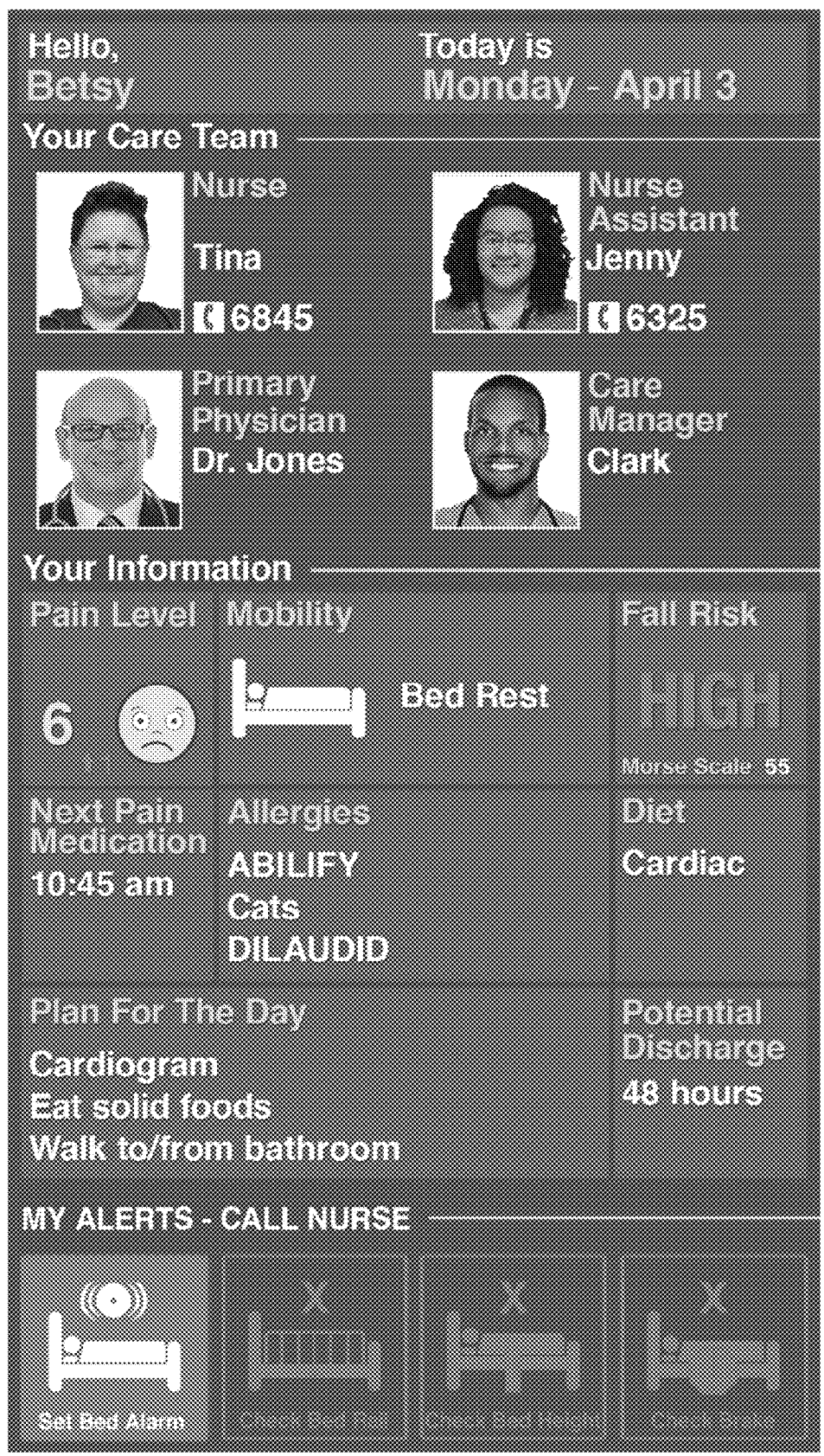
Figure 10D:
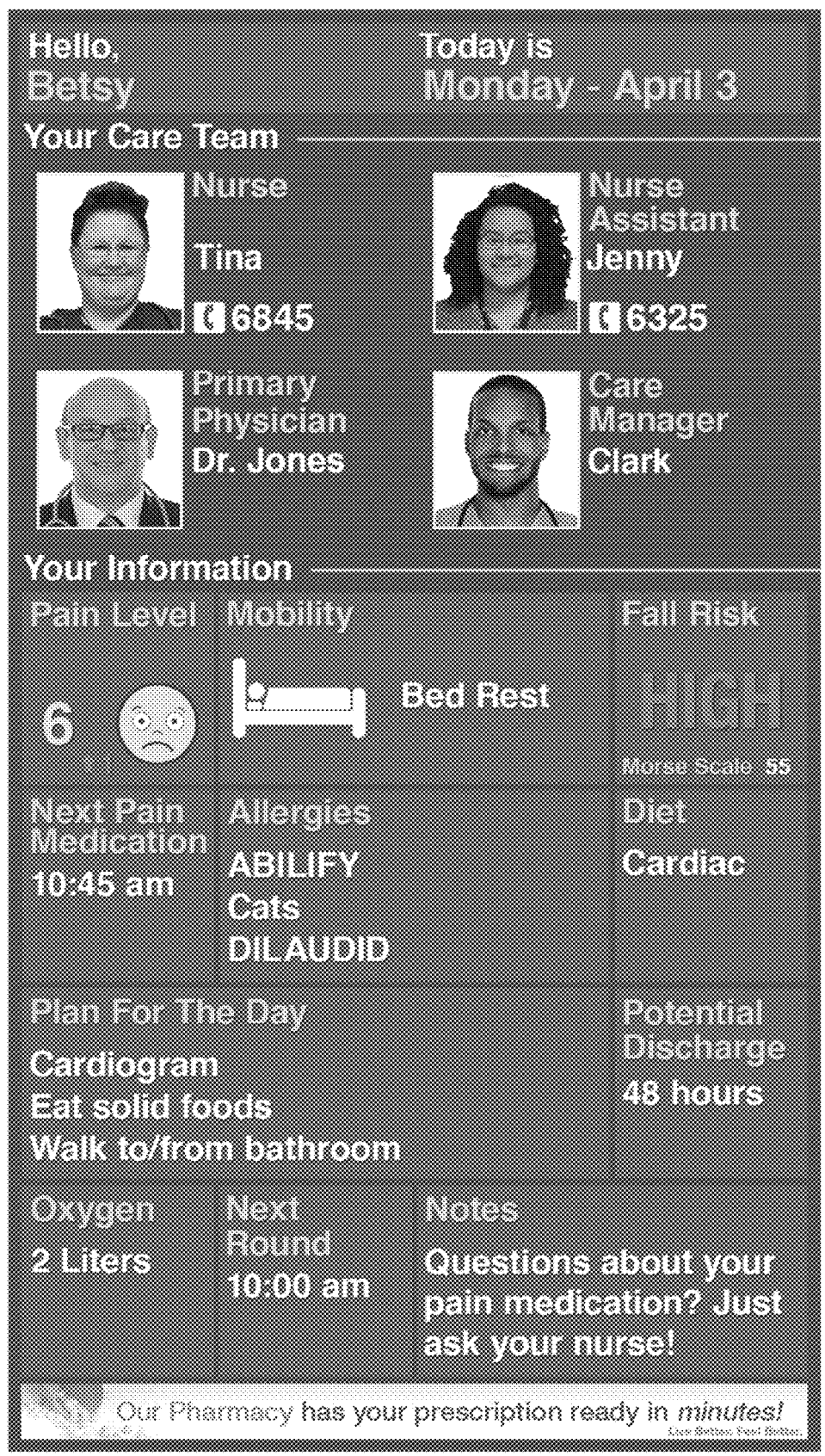

FIGS. 10C and 10D show additional examples of display content for an automated patient digital whiteboard. As shown in FIGS. 10C and 10D, the display content is similar to that shown in FIGS. 10A and 10B; however, FIGS. 10C and 10D show additional content. For example, the patient information portion includes a pain level including a trending pain indication, for example, an arrow and a number indicating a change in the pain level from the last measurement.

FIGS. 11A and 11B show examples of display content for a patient digital door board. As shown in FIGS. 11A and 11B, the patient digital door board includes a general message, a general alert, nurse information, a patient's preferred spoken and written language, various other specific alerts, and a room cleaning status. The examples shown in FIGS. 11A and 11B correspond to the patient location and content depicted in the examples of the automated patient digital whiteboard shown in FIGS. 10A and 10B, respectively. The example shown in FIG. 11C corresponds to the patient location and content depicted in the examples of the automated patient digital whiteboard shown in FIG. 10C.

The general message may be given, for example, alerting all visitors to see the nurse before entering the room. In addition, a general alert can be given to indicate conditions on patient contact. For example, the general alert can indicate whether a patient is in isolation or whether the patient is contagious and information reminders of protocols to use with patient. In this example, the general alert indicates the patient has been diagnosed with *Clostridium Difficile* and a corresponding care protocol including wash hands, use gloves and protective gowns, dispose of medical waste, disinfect surfaces, and limit patient transportation.

The patient digital door board also provides nurse information, such as the name and extension of the nurse on duty.

The patient digital door board also provides the patient's preferred spoken and written language indicated in this example as English.

The patient digital door board also provides various other specific alerts. In this example, the patient is indicated as a fall risk, has a latex allergy, is hearing impaired, is vision impaired, and that the room has been dimmed (e.g., indicating the patient is sleeping).

In the example given in FIG. 11A, the alerts also include that the bed alarm has not been set, the bed rail is not properly positioned, and the bed height needs to be adjusted. FIG. 11B shows an example of the display after the safety alert conditions have been satisfied.

Figure 11C:

FIG. 11C shows an additional example of the display content for a patient digital door board. In this example, the patient digital door board also provides various other specific alerts. In this example, the patient is indicated as a fall risk, has a latex allergy, is hearing impaired, is vision impaired, and an NPO indication, which means patient should receive nothing by mouth used, for example, when a patient is not allowed to eat or drink before surgery. In addition, a nurse with the clockwise arrow indicates a nurse round overdue. In addition, there is an indication when the room was last cleaned and by whom it was cleaned.

FIGS. 12A and 12B show examples of medical display content for a monitoring station digital board. In the example shown in FIGS. 12A and 12B, a monitoring station digital board provides information for the 5$^{th}$ floor, west wing nurse station. The display includes 28 rows and 8 columns. Each row corresponds to a patent room (e.g., rooms 5130-5157). The columns provide information such as room number, patient name, isolation status, fall risk, OOB status, assigned Nurse and corresponding contact number, and alerts.

The isolation status may indicate a type of restriction and/or protocol for the patient in the corresponding room, such as, for example, C. Diff, Airborne, droplet, and contact, among others. The fall risk can present HIGH or LOW to indicate whether the patient is a risk of falling. The OOB status may present a depiction to indicate patient status, such as a green bed to indicate the a patient is in bed, a yellow walking person icon to indicate a patient who is not a fall risk is out of bed, and a red waling icon to indicate a patient who is a fall risk and out of bed. The alarms column in this example provides information on a patient bed medical device. For example, icons are provided for bed alarm, bed rail, bed height, and bed brake. A red highlighted icon indicates an alarm, and a faint grey icon indicates no alarm status.

As a result, important information is quickly conveyed to and/or easily discernable by medical staff at the nurse station merely at a glance of the board.

In the example shown, the rooms are split between four nurses on duty (e.g., Tina, Betty, Rachael, and Danny). Rooms 5130, 5137, 5147, and 5156 (corresponding to Patient's Alex, Bobby, Kristen, Robert) have isolation protocols in place. Rooms 5130, 5133, 5135, 5140, 5145, 5150, and 5156 have high fall risk patients. Patient's Gerald, Travis, Pablo, David, Molly, Shannel and Linda are out of bed with Molly being a high fall risk possibly requiring immediate attention.

In addition, rooms 5130, 5133, and 5156 have bed alarms that are not armed.

In the example, shown in FIGS. 12A and 12B correspond to the example in FIGS. 10A &11A and 10B & 11B respectively. As can be seen in FIG. 12A patient Alex needs the bed alarm to be set, the bed rail to be properly positioned, and the bed height to be adjusted. FIG. 12B shows an example of the display after the safety alerts conditions have been satisfied.

FIG. 12C shows another example of medical display content for a monitoring station digital board. The medical display content in FIG. 12 is similar to that shown in FIGS. 12A and 12B, but provides slightly different information. For example, the patient name, nurse name, and contact columns have been removed. In addition, the content includes an indication of the next round time for a patient. The next round time indicates a future time at which a patient and/or room is due to be visited by the assigned nurse or an indication that the next round by a nurse for the patient and/or room is past due. The content also includes an indication of the next medication time for a patient. The next medication time indicates a future time at which a patient and/or room is due to be administered medication or an indication that the next medication time for the patient and/or room is past due. In addition, the OOB status includes an additional indication of a bed alarm condition (e.g., as shown for room number 5130 indicating the bed alarm for the patient has been tripped). In this example, the out of bed alarm is indicated by a reverse highlighting of the figure for the out of bed alert. Finally, the content includes a trending pain indication column indicating a pain level and a change is pain level from the last measurement with an arrow indicating the direction of the change or an indication that the pain level is an "initial pain level."

Alternative Embodiments

A processing device, as described above, may be implemented using one or more general-purpose or special purpose computer, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS (e.g., controllers, drivers, communication applications, etc.). It will be appreciated by one of ordinary skill in the art within the context of the applications described herein that, any or each of the above-mentioned functions may be implemented as a separate application or combined into a single application a required. The processing device also may access, store, manipulate, process, and create data in response to execution of the applications. For purpose of simplicity, the description of a processing device herein is used as singular; however, one skilled in the art will appreciated that a processing device may include multiple processing elements or devices and multiple types of processing elements or devices. For example, a processing device may include multiple processors or a processor, registers or buffers, a memory, and a controller. In addition, different processing configurations are possible, such as serial processors, parallel processors, a quad processor, a main processor and a display processor or caching processor, among others.

As used herein, a processing device operable or configured to implement a function or operation A includes a processor programmed to run specific software. In addition, a processing device operable or configured to implement a function or operation A, a function or operation B, and a function or operation C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software or applications implemented by the processing device may include a computer program, a piece of code, an instruction, or some combination thereof, for independently or collectively instructing or configuring the processing device to operate or perform functions as desired. Examples of software applications include: an operating system, drivers to control and/or operate various components of the user device (e.g., display, communications interface, input/output devices, etc.). The applications may be resident in the processing device, loaded from a storage device, or accessed from a remote location or a storage device (e.g., using a communications interface). Additional applications may be provided to implement on or more of the processes shown in any of FIG. 5, 6, 7, 8, or 9. Once the applications are loaded in or executed by the processing device, the processing device becomes a specific machine or apparatus configured or operable to perform functions. That is to say, an apparatus with a processing device programmed in a certain way is a physically different machine than that of an apparatus without such programming as its memory or storage elements are differently arranged and/or configured.

The software, applications, content, and data may be embodied permanently or temporarily in any type of machine, component, physical or virtual equipment, computer storage medium or device, or in a propagated signal wave capable of providing instructions or data to or being interpreted by the processing device. In particular, the software, applications, content, or data may be stored by one or more non-transitory computer storage devices or mediums including volatile and non-volatile memories that store digital data (e.g., a read only memory (ROM), a random access memory (RAM), a flash memory, a floppy disk, a hard disk, a compact disk, a tape, a DROM, a flip-flop, a register, a buffer, an SRAM, DRAM, SSD, PROM, EPROM, OPTROM, EEPROM, NOVRAM, or RAMBUS), such that if the storage device is read or accessed by the processing device, the specified steps, processes, and/or instructions are performed and/or data is accessed, processed, and/or stored. The computer storage device may include an I/O interface, such that data and applications may be loaded and stored in or accessed or read from the computer storage device allowing the applications, programming, and data to be used, updated, deleted, changed, augmented, or otherwise manipulated. The computer storage device may be removable, such as, for example, a disk drive, a card, a stick, or a disk that is inserted in or removed from the user device.

Specific functional programs, codes, code segments, and software for implementing the examples disclosed herein can be constructed by a programmer skilled in the art to which the examples pertain after receiving the guidance, direction, and teachings provided by the drawings and their corresponding descriptions as provided herein.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

Data and content may be exchanged between the various components of the system using at least one communications interface to send and receive information through the communication network paths. The communications network paths may be configured to send and receive signals (e.g., electrical, acoustic, electromagnetic, or optical) that convey or carry information representing various types of analog and/or digital data including programming, software, information, data, and other content, among others. For example, the communications paths may be implemented using various communications media and one or more networks comprising one or more network devices (e.g., network interface cards, fiber media converters, servers, routers, switches, hubs, bridges, repeaters, gateways, modems, processors, and storage devices). The one or more networks may include a local area network (LAN), a wide area network (WAN), an ETHERNET, a global area network (GAN), a cloud network, a plain old telephone service (POTS) network, a digital subscriber line (DSL) network, an integrated services digital network (ISDN), a synchronous optical network (SONNET)/SDH, Passive and Active Optical Networks (PON or AON), a packet switched network, V.92 telephone network modems, IRDA, USB, FIREWIRE, EIA RS-232, EIA-422, EIA-423, RS-449, RS-485, ITU, T1 and other T-carrier links, and E1 and other E-carrier links, varieties of 802.11, GSM Um radio interface, BLUETOOTH, IEEE 802.11x Wi-Fi, TRANSFERJET, ETHERLOOP, ARINC 818 AVIONICS Digital Video Bus, G.hn/G.9960, or a combination of two or more of these networks, to name a few examples.

In addition, the communications network paths may include one or more wireless links (e.g., microwave, radio, and satellite) that transmit and receive electromagnetic signals, such as, for example, radio frequency, infrared, and microwave signals, to convey information/data signals using any one of a number of communications protocols, for example, communications links may include IMT-2000, such as 2G (GSM, GPRS, EDGE, EDGE Evolution, CSD, HSCSD), 2.5G, 2.75G, 3G (W-CDMA, HSPDA, HSUPA, UMTS-TDD, FOMA), 4G, and IEEE 802.11 standards, such as Wi-Fi or WLAN, and HDTV and SDTV transmissions.

It will be appreciated that the examples given above are for illustrative purposes only, and that many different configurations, combinations of devices, and numbers of devices may be provided for any particular implementation of a system. For example, in FIG. 1 one monitoring station 111, two location 115, two patient device systems, two automated patient digital whiteboards, two patient digital door boards, and one monitoring station digital board are shown. However, it will be appreciated that in an actual implementation of the system, there may be many of these devices depending on the size and configuration of any medical facility in which the system is installed.

Similarly, although a single server and database are shown for the automated board controller in FIG. 1, in practice, multiple servers and processing devices, may be used and arranged in various configurations to receive, send, and process data for any number of reasons, such as redundancy, load balancing, volume, and processing requirements, to name but a few.

In addition, although the patient health device has been described as a patient bed, other patient health devices are contemplated and supported by the disclosure.

The various displays shown are also exemplary. Other types and/or arrangements of information may be shown consistent with the teachings provided herein.

The preceding detailed description is merely exemplary in nature and is not intended to limit the described embodiments (examples, options, etc.) or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described above are exemplary implementations provided to enable making or using the embodiments of the disclosure and are not intended to limit the scope of the disclosure. Furthermore, there is no intention to be bound by any expressed or implied theory presented in the preceding technical field, background, brief summary or the preceding detailed description. It is also to be understood that the specific devices and processes illustrated in the attached drawings, and described in this specification, are exemplary embodiments (examples), aspects and/or concepts. It is understood that "at least one" is equivalent to "a." The aspects (examples, alterations, modifications, options, variations, embodiments, and any equivalent thereof) are described with reference to the drawings; it should be understood that the descriptions herein show by way of illustration various embodiments in which claimed inventions may be practiced and are not exhaustive or exclusive. They are presented only to assist in understanding and teach the claimed principles. It should be understood that they are not representative of all claimed inventions. As such, certain aspects of the disclosure have not been discussed herein. That alternate embodiments may not have been presented for a specific portion of the invention or that further alternate embodiments not described that may be available for a portion is not to be considered a disclaimer of those alternate embodiments. It will be appreciated that many of those embodiments that are not described incorporate the same principles of the invention and others that are equivalent. Thus, it is to be understood that other embodiments may be utilized and functional, logical, organizational, and structural modifications may be made without departing from the scope and/or spirit of the disclosure.

A number of implementations of the techniques have been described. Nevertheless, it will be understood that various modifications may be made. For example, useful results still could be achieved if steps of the disclosed techniques were performed in a different order and/or if components in the disclosed systems were combined in a different manner and/or replaced or supplemented by other components. Accordingly, other implementations are within the scope of the following claims.

What is claimed is:

1. An automated medical display data communications network system configured for installation in a medical care facility that admits and discharges patients cared for by the medical care facility, wherein the medical care facility has a medical data communications network system that includes: a facility data communications network, a patient admission system configured to admit the patients cared for by the medical care facility, a patient health care records database configured to store data regarding patients admitted to the medical care facility, a patient monitoring nurse station configured to access and input patient data corresponding to the care and treatment of at least some of the patients admitted to the facility that are under the care of medical staff assigned to the at least some of the patients, and a plurality of patient beds assigned to the at least some patients, the automated medical display data communications network system comprising:

an automated medical display control (AMDC) device, the AMDC device comprising:
a network data communications system (NCS) including one or more data communications interfaces;
an AMDC storage device; and
an AMDC data processing device, communicatively coupled to the NCS and the AMDC storage device, wherein AMDC program instructions when executed by the AMDC data processing device cause the AMDC data processing device to:

(a) receive data packets from the facility data communications network including at least some patient data from the patient health care records database or the patient nurse monitoring station;
(b) receive data packets from a plurality of patient beds including patient bed data;
(c) store the received patient data and the received patient bed data in an AMDC patient database stored by the AMDC storage device;
(d) access a medical display template stored by the AMDC storage device, the medical display template corresponding to a location at the medical care facility;
(e) access the stored patient data and bed data from the AMDC patient database corresponding to the accessed medical display template;
(f) assemble a content payload from the accessed patient data and bed data corresponding to the accessed medical display template;
(g) generate a communication data package including the content payload; and
(h) transmit the communication data package through the NCS; and a medical display device (MDD) situated at the location at the medical care facility comprising:
an MDD display; and
a MDD control device communicatively coupled to the MDD display comprising:
an MDD data communication interface;
an MDD storage device; and
an MDD data processing device communicatively coupled to the MDD data communication interface and the MDD storage device, wherein MDD program instructions when executed by the MDD data processing device cause the MDD data processing device to:
(i) determine the MDD communication interface has received the communication data package;
(j) determine the communication data package received by the MDD communications interface is addressed to the MDD;
(k) unpack the communication data package to access the content payload; and
(l) render the content payload on the MDD display as a medical display board customized for a location of the MDD corresponding to the location at the medical care facility, the medical display board presenting information corresponding to the accessed patient data and bed data, wherein the automated medical display data communications network system is provided in addition to the medical data communications network, the patient admission system, the patient health care records database, and the patient monitoring nurse station of the medical care facility, and wherein the AMDC device is configured to automatically continue to analyze the AMDC patient database stored by the AMDC storage device and implement an AMDC patient safety protocol that is supplementary to any patient safety protocol or measure implemented by the medical care facility.

2. The automated medical display data communications network system of claim 1, wherein implementation of the AMDC patient safety protocol is automatically implemented by the AMDC processing device based on the accessed patient and bed data without any direct interaction by medical staff of the facility with the AMDC device.

3. The automated medical display data communications network system of claim 1, wherein generating the communication data package including the content payload is independent or agnostic of any data protocols of the medical data communications network system including: the patient admission system, the patient health care records database, the patient monitoring nurse station, and the plurality of patient beds.

4. The automated medical display data communications network system of claim 1, wherein the AMDC program instructions when executed by the AMDC data processing device further cause the AMDC data processing device to:
analyze the patient data and the patient bed data stored in the AMDC patient database;
determine that a reading or a setting of a patient bed assigned to a patient in combination with patient data corresponding to the patient assigned to the patient bed indicates a condition affecting safety of the patient assigned to the patient bed; and
provide an indication corresponding to the condition affecting the safety of the patient assigned to the patient bed as content in the content payload.

5. The automated medical display data communications network system of claim 4, wherein the condition affecting the safety of the patient includes one of: a failure to arm a bed exit alarm; an improper bed height; a patient is out a patient bed; a failure to position a bed rail; and a failure to set a bed brake.

6. The automated medical display data communications network system of claim 4, wherein the patient data corresponding to the patient assigned to the patient bed includes identification that the patient assigned to the patient bed is at risk of fall.

7. The automated medical display data communications network system of claim 4, wherein the reading or setting is one of a bed exit alarm, a bed height, a weight measurement, a rail position, and a bed brake.

8. The automated medical display data communications network system of claim 4, wherein the reading or setting is an angle of the bed, the patient data corresponding to the patient assigned to the patient bed includes intubation and the condition affecting the safety of the patient includes an improper Fowler position of the patient's bed.

9. The automated medical display data communications network system of claim 4, wherein the patient data corresponding to the patient assigned to the patient bed includes identification that the patient assigned to the patient bed is at risk of fall, the reading is a weight measurement, and the condition affecting the patient's safety is that the patient assigned to the patient bed is out of the assigned patient bed.

10. The automated medical display data communications network system of claim 4, wherein the AMDC program instructions when executed by the AMDC data processing device further cause the AMDC data processing device to:
further analyze the patient data and the patient bed data stored in the AMDC patient database;
determine that the reading or the setting of the patient bed assigned to the patient in combination with the patient data corresponding to the patient assigned to the patient bed indicates the condition affecting safety of the patient assigned to the patient bed is removed; and
provide an indication of the removal of the condition affecting the safety of the patient assigned to the patient bed as content in the content payload.

11. The automated medical display data communication network system of claim 1 further comprising a plurality of MDDs, wherein each of the plurality of MDDs is configured to present the accessed patient data and bed data corresponding to a location of the MDD at the medical care facility.

12. The automated medical display data communications network system of claim 1, wherein the medical display template has corresponding, customizable display widgets that associate data from the AMDC storage device to the medical display board corresponding to the medical display template allowing the AMDC processing device to assemble the content payload.

13. The automated medical display data communications network system of claim 1, wherein the medical display template corresponding to a location at the medical care facility provides a medical communication interface customized for a location at the medical care facility including one of: a patient room; outside of the patient room; and the patient monitoring nurse station.

14. The automated medical display data communications network system of claim 1, wherein the AMDC data processing device is configured to repeat processes (a)-(h) and the MDD data processing device is configured to repeat processes (i)-(l) to provide continually updated information for presentation on the MDD display.

15. The automated medical display data communications network system of claim 1, wherein the AMDC program instructions when executed by the AMDC data processing device further cause the AMDC data processing device to:
    determine information presented by the medical display template;
    request data from the medical data communications network system corresponding to the determined information; and
    receive data in response to the request; and
    stored the received data in the AMDC patient database.

16. An automated medical display data communications network system configured for installation in a medical care facility that admits and discharges patients cared for by the medical care facility, wherein the medical care facility has a medical data communications network system that includes: a facility data communications network, a patient admission system configured to admit the patients cared for by the medical care facility, a patient health care records database configured to store data regarding patients admitted to the medical care facility, a patient monitoring nurse station configured to access and input patient data corresponding to the care and treatment of at least some of the patients admitted to the facility that are under the care of medical staff assigned to the at least some of the patients, and a plurality of patient beds assigned to the at least some patients, the automated medical display data communications network system comprising:
    an automated medical display control (AMDC) device, the AMDC device comprising:
        a network data communications system (NCS) including one or more data communications interfaces;
        an AMDC storage device; and
        an AMDC data processing device, communicatively coupled to the NCS and the AMDC storage device, wherein AMDC program instructions when executed by the AMDC data processing device cause the AMDC data processing device to:
            (a) receive data packets from the facility data communications network including at least some patient data from the patient health care records database or the patient nurse monitoring station;
            (b) receive data packets from a plurality of patient beds including patient bed data;
            (c) store the received patient data and the received patient bed data in an AMDC patient database stored by the AMDC storage device;
            (d) access a plurality of medical display templates stored by the AMDC storage device, wherein each medical display template is customized for a type of location at the medical facility; and for each accessed template:
            (e) access the stored patient data and bed data from the AMDC patient database corresponding to the accessed medical display template;
            (f) assemble a content payload from the accessed patient data and bed data corresponding to the accessed medical display template;
            (g) generate a communication data package including the content payload; and
            (h) transmit the generated communication data package via the NCS; and
    a plurality of medical display devices (MDDs) situated at different locations of the medical care facility, each MDD comprising:
    an MDD display; and
    a MDD control device communicatively coupled to the MDD display comprising:
        an MDD data communication interface;
        an MDD storage device; and
        an MDD data processing device communicatively coupled to the MDD data communication interface and the MDD storage device, wherein MDD program instructions when executed by the MDD data processing device cause the MDD data processing device to:
            (i) determine the MDD communication interface has received a communication data package;
            (j) determine the communication data package received by the MDD communications interface is addressed to the MDD;
            (k) unpack the determined communication data package to access the content payload; and
            (l) render the content payload on the MDD display as a medical display board customized for a location of the MDD corresponding to the location at the medical care facility, the medical display board presenting information corresponding to the accessed patient data and bed data,
    wherein the automated medical display data communications network system is provided in addition to the medical data communications network system, the patient admission system, the patient health care records database, and the patient monitoring nurse station of the facility, and wherein each of the plurality of templates provides a different presentation or arrangement of information based on the accessed patient data and bed data from the AMDC patient database and the different presentation or arrangement of information is customized for the location of the MDD in the medical care facility.

17. The automated medical display data communications network system of claim 16, wherein the AMDC device is configured to automatically and continuously analyze the AMDC patient database stored by the AMDC storage device and implement an AMDC patient safety protocol that is supplementary to any patient safety protocol or measure implemented by the medical care facility and implementation of the AMDC patient safety protocol is automatically implemented by the AMDC processing device without any direct interaction by the AMDC by medical staff of the facility with the AMDC device.

18. The automated medical display data communications network system of claim 16, wherein the AMDC program instructions when executed by the AMDC data processing device further cause the AMDC data processing device to:
- analyze the patient data and the patient bed data stored in the AMDC patient database;
- determine that a reading or a setting of a patient bed assigned to a patient in combination with patient data corresponding to the patient assigned to the patient bed indicates a condition affecting safety of the patient assigned to the patient bed; and
- provide an indication corresponding to the condition affecting the safety of the patient assigned to the patient bed as content in the content payload.

19. The automated medical display data communications network system of claim 18, wherein the AMDC program instructions when executed by the AMDC data processing device further cause the AMDC data processing device to:
- further analyze the patient data and the patient bed data stored in the AMDC patient database;
- determine that the reading or the setting of the patient bed assigned to the patient in combination with the patient data corresponding to the patient assigned to the patient bed indicates the condition affecting safety of the patient assigned to the patient bed is removed; and
- provide an indication the removal of the condition affecting the safety of the patient assigned to the patient bed as content in the content payload.

20. The automated medical display data communications network system of claim 16, wherein the medical display template corresponding to a location at the medical care facility provides a medical communication interface customized for a location at the medical care facility including one of: a patient room; the outside of the patient room; and the patient monitoring nurse station.

* * * * *